United States Patent
Leufkens

(10) Patent No.: US 9,616,135 B2
(45) Date of Patent: Apr. 11, 2017

(54) 2-IMINOBIOTIN FORMULATIONS AND USES THEREOF

(71) Applicant: Neurophyxia B.V., 's-Hertogenbosch (NL)

(72) Inventor: Paul W. T. J. Leufkens, 's-Hertogenbosch (NL)

(73) Assignee: Neurophyxia B.V., Hertogenbosch (NL)

( * ) Notice: Subject to any disclaimer, the term of this patent is extended or adjusted under 35 U.S.C. 154(b) by 0 days.

(21) Appl. No.: 14/676,419

(22) Filed: Apr. 1, 2015

(65) Prior Publication Data

US 2015/0202303 A1    Jul. 23, 2015

Related U.S. Application Data

(62) Division of application No. 13/700,090, filed as application No. PCT/NL2011/050366 on May 26, 2011, now Pat. No. 9,023,878.

(30) Foreign Application Priority Data

May 26, 2010 (EP) .................................. 10163925

(51) Int. Cl.
| | |
|---|---|
| A61K 31/4188 | (2006.01) |
| A61K 47/40 | (2006.01) |
| A61K 9/00 | (2006.01) |
| A61K 31/724 | (2006.01) |
| A61K 47/12 | (2006.01) |
| A61K 47/48 | (2006.01) |
| B82Y 5/00 | (2011.01) |

(52) U.S. Cl.
CPC ........... *A61K 47/40* (2013.01); *A61K 9/0019* (2013.01); *A61K 31/4188* (2013.01); *A61K 31/724* (2013.01); *A61K 47/12* (2013.01); *A61K 47/48969* (2013.01); *B82Y 5/00* (2013.01)

(58) Field of Classification Search
CPC .............................. A61K 31/4188; A61K 47/40
See application file for complete search history.

(56) References Cited

U.S. PATENT DOCUMENTS

| 6,894,069 B2 | 5/2005 | Peeters et al. |
| 9,023,878 B2 * | 5/2015 | Leufkens ............. A61K 9/0019 514/388 |
| 2013/0143936 A1 | 6/2013 | Leufkens |

FOREIGN PATENT DOCUMENTS

| CN | 1333651 A | 1/2002 |
| WO | 00/42849 | 7/2000 |
| WO | 01/74351 A1 | 10/2001 |
| WO | 2011/149349 A1 | 12/2011 |

OTHER PUBLICATIONS

Groenendaal et al. Early Human Development, 2009, vol. 85, pp. 73-76 (Published Online Jan. 6, 2009).*
PCT International Search Report, PCT/NL2011/050366 dated Sep. 26, 2011.
Text for Chinese Office Action in Application 201180034057.8 dated Jan. 14, 2014, 4 pages.
Debillon et al., Whole-body cooling after perinatal asphyxia: a pilot study in term neonates, Development medicine and child neurology, 2003, pp. 17-23, vol. 45.
Van Dyke, et al., The effect of administration of 2-iminobiotin at birth on growth rates, morbidity and mortality in piglets under farm conditions, Livestock Science, 2008, pp. 129-136, vol. 115, Science Direct, Elsevier.
Dijk et al., The effect of administration of 2-iminobiotin at birth on growth rates, morbidity and mortality in piglets under farm conditions, 8 pages, Livestock Science, Jun. 23, 2007 pp. 129-136, No. 115, Elsevier Inc.
Loftsson, Cyclodextrins, 36 pages, Jornal of Pharmaceutical Science, May 5, 2004, vol. 93, No. 5.

* cited by examiner

*Primary Examiner* — James D Anderson
(74) *Attorney, Agent, or Firm* — Traskbritt P.C.

(57) ABSTRACT

The disclosure relates to improving the aqueous solubility of 2-iminobiotin. In a particular aspect, the disclosure pertains to formulations suitable for administration of 2-iminobiotin to mammals suffering from disorders or conditions that benefit from that administration.

12 Claims, 1 Drawing Sheet

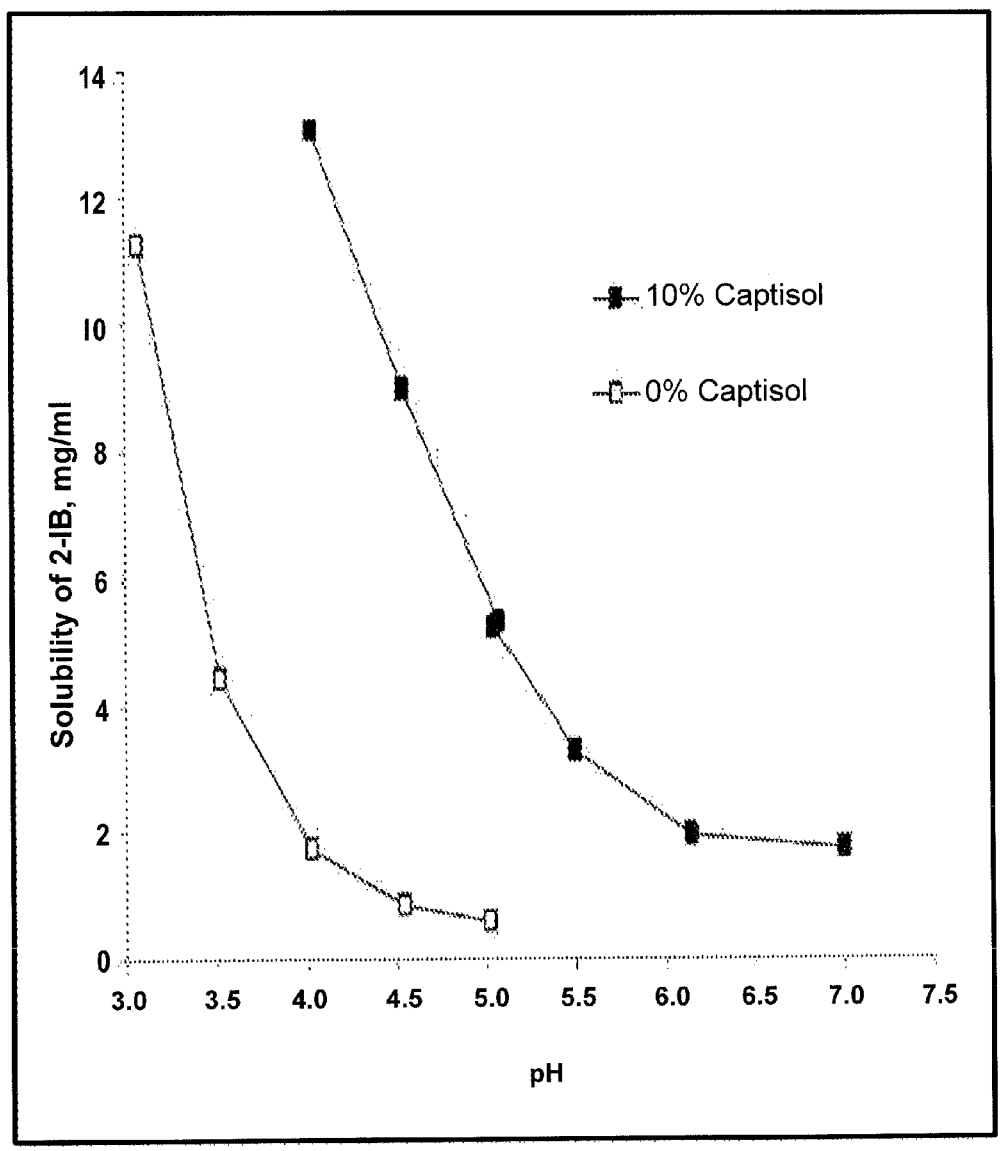

2-IMINOBIOTIN FORMULATIONS AND USES THEREOF

CROSS-REFERENCE TO RELATED APPLICATIONS

This application is a divisional of co-pending U.S. patent application Ser. No. 13/700,090, filed Jan. 31, 2013, now U.S. Pat. No. 9,023,878, which is a national phase entry under 35 U.S.C. §371 of International Patent Application PCT/NL2011/050366 filed on May 26, 2011, published in English as International Patent Publication No. WO 2011/149349 A1, which claims the benefit under Article 8 of the Patent Cooperation Treaty to European Patent Application Serial No. 10163925.0, filed May 26, 2010, the disclosure of each of which is hereby incorporated herein in its entirety by this reference.

TECHNICAL FIELD

The application relates to pharmaceutics and improving the aqueous solubility of 2-iminobiotin. In a particular aspect, the application pertains to formulations suitable for administration of 2-iminobiotin to mammals suffering from disorders or conditions that benefit from that administration.

BACKGROUND

It has been reported that 2-iminobiotin can be used to prevent and/or treat the effects of perinatal asphyxia (hypoxia-ischemia) in neonates (U.S. Pat. No. 6,894,069, which is hereby incorporated by reference in its entirety). In particular, in-vivo studies involving piglets demonstrated that 2-iminobiotin is more effective in preventing and/or treating these effects than either allopurinol or deferoxamine.

The low solubility of 2-iminobiotin at physiological pH, however, limits its usefulness as a therapeutic agent. There exists a need in the art for improved 2-iminobiotin formulations and methods of increasing its solubility. The disclosure provides such improvements.

BRIEF SUMMARY

Provided is an aqueous, soluble formulation of 2-iminobiotin (2-IB), or a derivative thereof, having a pH between around 3 and around 7, and comprising around 1 mg/ml or more of 2-iminobiotin, or a derivative thereof, and between around 2.5 to around 40% of a substituted beta-cyclodextrin.

In some embodiments, the formulation has a pH between around 4 and around 7, and comprising around 2 mg/ml or more of 2-iminobiotin, or a derivative thereof, and around 2.5 to around 20% of a substituted beta-cyclodextrin, preferably selected from sulfobutyl-ether-beta-cyclodextrin (SBE-CD) and hydroxypropyl-beta-cyclodextrin (HP-CD).

In some embodiments, the formulation has a pH between around 4 and around 5, and comprising around 3.5 mg/ml or more of 2-iminobiotin and between around 2.5 to around 40, preferably between around 5 to around 10% of a substituted beta-cyclodextrin, preferably selected from sulfobutyl-ether-beta-cyclodextrin (SBE-CD) and hydroxypropyl-beta-cyclodextrin (HP-CD).

In some embodiments, the formulation has a pH between around 4 and around 5 and comprising between around 3 to around 5 mg/ml, preferably between around 4 to around 5 mg/ml of 2-iminobiotin, and around 2.5 to around 5% of a substituted beta-cyclodextrin, preferably selected from sulfobutyl-ether-beta-cyclodextrin (SBE-CD) and hydroxypropyl-beta-cyclodextrin (HP-CD).

Preferably, the formulation further comprises citric acid or a deprotonated version thereof (citrate) as a solubility enhancer.

In some embodiments, a soluble formulation of 2-iminobiotin, or a derivative thereof, is provided having a pH around 5 and comprising around 3 mg/ml or more of 2-iminobiotin and around 3 to around 40%, preferably around 5% of SBE-CD.

In some embodiments, a soluble formulation of 2-iminobiotin, or a derivative thereof, is provided having a pH around 4, and comprising around 3 mg/ml or more of 2-iminobiotin and around 5 to around 40% of HP-CD. Preferably the formulation comprises from around 5 to around 20% HP-CD.

In some embodiments, the formulations further comprise NaCl, preferably between 0.1 and 2%, more preferably between 0.5 and 0.8% as an isotonicity agent.

Also provided is an aqueous, soluble formulation of 2-iminobiotin (2-IB), or a derivative thereof, having a pH between around 3 and around 7, and comprising around 0.75 mg/ml or more of 2-iminobiotin and citric acid, a deprotonated version thereof, or a mixture thereof. Surprisingly, 2-IB was found to have a higher solubility in citric acid buffer. As used herein, citric acid buffer refers to citric acid, a deprotonated version thereof, or a mixture thereof and includes aqueous solutions of, e.g., sodium citrate dehydrate.

Preferably, the formulation has a pH between around 3 and around 7, preferably between around 3 and around 6, more preferably between around 3.5 and around 4.5, even more preferably around pH 4, and comprises between around 0.5 mg/ml and around 10 mg/ml, preferably between around 0.5 mg/ml and around 5 mg/ml of 2-iminobiotin, more preferably between around 0.5 mg/ml and around 2 mg/ml, even more preferably between around 0.5 mg/ml and around 1 mg/ml of 2-iminobiotin and citric acid, a deprotonated version thereof, or a mixture thereof. Preferably, the formulations comprise between about 1 to about 40, about 5 to about 30, preferably about 10 to about 20, more preferably about 12.5 to about 17.5 mM, even more preferably around 15 mM citric acid, a deprotonated version thereof, or a mixture thereof. It is clear to a skilled person that the amount of buffer can be adjusted to obtain the desired pH level. Preferably, the formulation comprises between 0.1 and 2% of NaCl as an isotonicity agent, more preferably between 0.5 and 1.5%. An exemplary formulation has a concentration of about 0.9% NaCl.

Preferably, the formulation is suitable for administration to a human neonate. Preferably, the 2-iminobiotin, or a derivative thereof, remains soluble for at least 3 days at 5° C. In some embodiments, the 2-iminobiotin, or a derivative thereof, remains soluble for at least 0.5, 1, 1.5, 2, or 3 years at 5° C.

Also provided are 2-iminobiotin formulations, or a derivative thereof, as described herein for use in treating the effects of complications during childbirth, preferably for treating perinatal asphyxia or the risk thereof, in a neonate. In some embodiments, the formulation is administered to the neonate. In some embodiments, the formulation is administered to the mother of the neonate prior to and/or during labor.

Further provided is the use of 2-iminobiotin, or a derivative thereof, for use in treating the effects of complications during childbirth, preferably for treating perinatal asphyxia or the risk thereof, wherein the treatment is combined with subjecting the neonate to hypothermia.

Also provided are methods for treating the effects of complications during childbirth in a neonate, comprising administering a therapeutically effective amount of the formulation described herein to the neonate in need thereof. In some embodiments, the formulation is also administered, or administered instead, to the mother of the neonate in need thereof prior to and/or during labor. Preferably, the complication is perinatal asphyxia or the risk thereof.

Further provided are methods for treating the effects of complications during childbirth in a neonate, comprising administering a therapeutically effective amount of 2-iminobiotin, or a derivative thereof, to the neonate in need thereof and subjecting the neonate to hypothermia. In some embodiments, the 2-iminobiotin, or a derivative thereof, is also administered, or administered instead, to the mother of the neonate in need thereof prior to and/or during labor. Preferably, the complication is perinatal asphyxia or the risk thereof. Preferably, the 2-iminobiotin, or a derivative thereof, is in a formulation as described herein.

Still further provided is the use of 2-iminobiotin, or a derivative thereof, for the manufacture of a medicament with a formulation as described herein for treating the effects of complications during childbirth. In some embodiments, the treatment is combined with subjecting the neonate to hypothermia. Preferably, the complication is perinatal asphyxia. The formulations are also provided for use in treating a disease or disorder responsive to 2-iminobiotin treatment.

Further provided are methods for preparing the formulations described herein comprising the steps of dissolving 2-iminobiotin, or a derivative thereof, in an aqueous solution comprising a beta-cyclodextrin followed by adjusting the pH of the solution resulting in a 2-iminobiotin solution, or a derivative thereof. Preferably, the pH of the 2-iminobiotin solution is adjusted using citric acid. Preferably, the pH is adjusted to between around 3 to around 7. Preferably, the aqueous solution is between pH 4 and 6.6. Preferably, the beta-cyclodextrin is SBE-CD. Preferably, the aqueous solution comprises NaCl. Preferably, the aqueous solution comprises citric acid or a deprotonated version thereof.

Preferably, 2-IB derivatives are 2-iminobiotin carboxy derivatives. Preferably, 2-iminobiotin carboxy derivatives are 2-iminobiotin hydrazide and/or 2-iminobiotin N-hydroxysuccinimide ester. Preferably, the formulations described herein comprise 2-IB.

2-iminobiotin (2-IB) has poor water solubility and, thus, is difficult to formulate as an aqueous solution for administration (see Comparative Examples). In accordance with the disclosure, it has been found that the water-solubility of 2-IB may be sufficiently increased to allow it to be formulated as an aqueous solution by adding 2-IB to a citric acid/citrate buffer and/or a substituted beta-cyclodextrin. The terms "insoluble" and "poorly soluble" are used herein to characterize a drug in respect of its water solubility. As used herein, "insoluble" refers to solubility of less than 0.1 mg/ml and "poorly soluble" refers to solubility in the range of 0.1 to 1 mg/ml.

The solubility of 2-IB is pH dependent. The solubility of 2-IB in water is around 0.34 mg/ml at pH 7.4, around 0.59 mg/ml at pH 5, and around 4.5 mg/ml at pH 3.5. As administration of low pH solutions intramuscularly can illicit pain in a subject (R. Rukwied, *J. Pain.* 2007 May; 8(5):443-51) and can lead to metabolic acidosis when administered as a continuous intravenous infusion (M. C. Federman, *Clinical Neuropharmacology* 2009 November-December; 32(6):340-1), one object of the disclosure is to provide 2-IB formulations with a pH and 2-IB concentration suitable for administration in a therapeutic setting.

In the treatment of conditions associated with, e.g., asphyxia or hypoxia, a therapeutically effective amount of drug needs to be administered within a specific period of time in order to be effective. With the formulations present in the prior art, a significant volume of 2-IB solution needs to be administered due to the low solubility of 2-IB. The larger the volume of solution needed to be administered, the longer the time before a therapeutically effective concentration in the body is reached. For some applications, such as the treatment of neonates, the volume of solution needed to be administered within the therapeutic window is a limiting factor. Typically, the maximum amount of fluid to be considered, save to administer intravenously to an asphyxiated term neonate, is 50 ml/kg/day. By increasing the solubility of 2-IB, the drug can be more quickly administered and in a lower volume.

2-IB formulations should, optimally, be stable for long periods of time, preferably for several years. In addition, the formulations should not precipitate when stored in a cool environment, such as 5 degrees C.

Various drug formulations were produced using a variety of solvents, co-solvents, surfactants, cyclodextrins, and other excipients. The solubility of 2-IB was either low or the formulation was toxic (see Comparable Examples). Surprisingly, formulating 2-IB with more than 1% substituted beta-cyclodextrins, in particular with 2.5% or more, and/or with citric acid buffers, provided solutions with increased solubility at suitable pH levels.

The formulations described herein are suitable for preparing pharmaceutical solutions of 2-IB ($C_{10}H_{17}N_3O_2S$) as well as 2-IB derivatives. 2-IB derivatives include 2-iminobiotin carboxy derivatives. 2-iminobiotin carboxy derivatives have been shown to be inhibitors of iNOS, indicating that the free carboxyl group of 2-IB is not required for iNOS inhibition (S. J. Sup et al., *Biochem. and Biophys. Res. Comm.* 1994 204:962-968). Preferably, 2-iminobiotin carboxy derivatives are 2-iminobiotin hydrazide and/or 2-iminobiotin N-hydroxysuccinimide ester. Preferably, the formulations described herein comprise 2-IB.

Cyclodextrins vary in structure and properties. For example, the size (e.g., diameter, and depth) and functionality (e.g., hydrophobicity, charge, reactivity and ability to hydrogen bond) of the hydrophobic cavity varies among substituted and unsubstituted alpha-, beta- and gamma-cyclodextrins. The term "cyclodextrin" refers to a compound including cyclic alpha-linked D-glucopyranose units. Alpha-cyclodextrin refers to a cyclodextrin with six cyclic, linked D-glucopyranose units, beta-cyclodextrin has seven cyclic, linked D-glucopyranose units, and gamma-cyclodextrin has eight cyclic, linked D-glucopyranose units. These cyclic, linked D-glucopyranose units define a hydrophobic cavity, and cyclodextrins are known to form inclusion compounds with other organic molecules, with salts, and with halogens, either in the solid state or in aqueous solutions. Typically, a cyclodextrin selected for a formulation has a size and functionality that is suitable for the target component and the other components of the formulation. Unfortunately, there are many drugs for which cyclodextrin complexation either is not possible or produces no apparent advantages (J. Szejtli, *Cyclodextrins in Drug Formulations: Part II, Pharmaceutical Technology,* 24-38, August, 1991).

Substituted cyclodextrins can include as side chains any organic moiety or a hetero-organic moiety. Preferred cyclodextrins include substituted beta-cyclodextrins that have been alkylated, hydroxyalkylated, or reacted to form a sulfoalkyl ether. Preferred beta-cyclodextrins include hydroxypropyl-beta-cyclodextrin, e.g., (S)-2-hydroxypropyl-beta-cyclodextrin, 2-O—[(S)-2'-hydroxylpropyl]-beta-cyclodextrin, 2-O—[(R)-2'-hydroxylpropyl]-beta-cyclodextrin, 6-O—[(S)-2'-hydroxylpropyl]-beta-cyclodextrin, 2-O—[(R)-2',3'-hydroxylpropyl]-beta-cyclodextrin; hydroxyethyl-beta-cyclodextrin; carboxymethyl-beta-cyclodextrin; carboxymethyl-ethyl-beta-cyclodextrin; diethyl-beta-cyclodextrin; dimethyl-beta-cyclodextrin; glucosyl-beta-cyclodextrin; hydroxybutenyl-beta-cyclodextrin; maltosyl-beta-cyclodextrin; and sulfobutylether-beta-cyclodextrin. For the present formulations and methods, it is believed that substituted beta-cyclodextrins, such as, e.g., hydroxypropyl-beta-cyclodextrin and sulfobutylether-beta-cyclodextrin, have a size and functionality that complement the other components of the formulation. More preferably, the cyclodextrin is sulfobutylether-beta-cyclodextrin ("SBE-CD").

Two types of substituted beta-cyclodextrins were tested in the 2-IB formulations. Both markedly increased the solubility of 2-IB. (See Examples.) Sulfobutylether-beta-cyclodextrin (SBE-CD) is a commercially available polyanionic beta-cyclodextrin derivative with a sodium sulfonate salt separated from the hydrophobic cavity by a butylether spacer group, or sulfobutylether (CAPTISOL® is the trade name for hepta-substituted sulfobutylether-beta-cyclodextrin available from CyDex Inc.). Hydroxypropyl-beta-cyclodextrin (HP-CD) is a commercially available beta-cyclodextrin derivative available from Roquette Pharma S.A. as KLEPTOSE®. Cyclodextrins are further described in U.S. Pat. Nos. 5,134,127 and 5,376,645, the entire contents of which are hereby incorporated by reference.

The 2-IB formulations disclosed herein may be formed of dry physical mixtures of 2-IB and the substituted beta-cyclodextrin or dry inclusion complexes thereof, which, upon addition of water, are reconstituted to form an aqueous formulation. Alternatively, the aqueous formulation may be freeze-dried and later reconstituted with water.

In some embodiments, the 2-IB formulations disclosed herein are in the form of an aqueous solution and include an acid buffer to adjust the pH within the range from about 4 to about 7. Examples of acid buffers suitable for use herein include acids such as hydrochloric acid, sulfuric acid, phosphoric acid, hydrobromic acid and the like, and organic acids such as oxalic acid, maleic acid, fumaric acid, lactic acid, malic acid, tartaric acid, citric acid, benzoic acid, acetic acid, methanesulfonic acid, toluenesulfonic acid, benzene sulfonic acid, ethane sulfonic acid, and the like. Acid salts of the above acids may be employed as well. Preferably, the formulation comprises sufficient citric acid and/or sodium citrate or other citrate salt to reach the desired pH. In some embodiments, the formulations comprise between 1 and 25 mM citric acid. In some embodiments, the formulations comprise between 0.1 and 5 mM sodium citrate. In some embodiments, the formulations comprise at least 20 mM citric acid/citrate. Preferably, the formulations comprise between about 1 to about 40, about 5 to about 30, preferably about 10 to about 20, more preferably about 12.5 to about 17.5 mM citric acid, a deprotonated version thereof, or a mixture thereof. Preferably the formulations comprise around 15 mM citric acid, a deprotonated version thereof, or a mixture thereof.

The 2-IB formulations disclosed herein may be prepared as follows: citric acid or other acid buffer is dissolved in water for injection. The substituted beta-cyclodextrin (preferably SBE-CD), if used, is dissolved in the acid buffer-water solution. 2-IB is then dissolved in the solution. Alternatively, the substituted beta-cyclodextrin (preferably SBE-CD), if used, is dissolved in a water solution, and 2-IB is then dissolved in the solution. The pH is adjusted to within the range from about 3 to about 6.

The formulations are preferably prepared and packaged for use as sterile and pyrogen-free. For example, the resulting solution may be aseptically filtered, e.g., through a 0.22-micron membrane filter and filled into sterile vials. The vials are stopped and sealed and may be terminally sterilized. The solutions may also be provided in ampoules, syringes, IV bags, or other dispensers. Preferably, the formulation is provided in a single dose unit. The solutions can be autoclaved without affecting 2-IB stability (Table 24).

It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

2-IB formulations intended for pediatric administration preferably do not comprise contraindicated excipients (e.g., lactic acid, docusate sodium, propylene glycol, etc.). Preferably, formulations for pediatric administration also do not contain benzyl alcohol, propyl gallate, polysorbate 20, 40 or 60, sodium benzoate, thimerosal, peanut oil, or boric acid. It is within the purview of one skilled in the art to select suitable additional agents.

Preferably, the 2-IB formulations are isotonic. In some embodiments, the 2-1B formulations further comprise NaCl, preferably between 0.1 and 0.9%, more preferably between 0.2 and 0.9%. In some embodiments, the 2-IB formulations further comprise sugars, such as glucose, lactose, or mannitol, preferably between 1 and 5%, more preferably between 2 and 5%. Preferably, in particular with a pediatric formulation, the sugar is glucose. The formulation may comprise a combination of NaCl and sugar in such an amount that the formulation is isotonic.

The disclosure provides solutions and dosage forms of 2-IB for, preferably, parenteral administration. "Parental administration" as used herein refers to modes of administration including, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Preferably, the formulations are administered intravenously.

The formulations may be provided in vials, ampoules, syringes, IV bags, or other dispensers. They may be administered directly to a subject or further diluted. A dose-concentrate of a provided formulation can be in a sealed container holding an amount of the formulation to be employed over a standard treatment interval such as immediately upon dilution, or up to 24 hours after dilution, as necessary. A solution for intravenous administration can be prepared, for example, by adding a dose-concentrate formulation to a container (e.g., glass or plastic bottles, vials, ampoules) in combination with diluent so as to achieve desired concentration for administration.

Addition of aqueous solvent to a liquid dose concentrate may be conveniently used to form unit dosages of liquid pharmaceutical formulations by removing aliquot portions or entire contents of a dose concentrate for dilution. Dose concentrate may be added to an intravenous (IV) container containing a suitable aqueous solvent. Useful solvents are standard solutions for injection (e.g., 5% dextrose, saline, lactated ringer's, or sterile water for injection, etc.). Typical unit dosage IV bags are conventional glass or plastic containers having inlet and outlet means and having standard (e.g., 25 mL, 50 mL, 100 mL and 150 mL) capacities.

In other embodiments, it may be desirable to package a provided dosage form in a container to protect the formulation from light until usage. In some embodiments, use of such a light-protective container may inhibit one or more degradation pathways. For example, a vial may be a light container that protects contents from being exposed to light. Additionally and/or alternatively, a vial may be packaged in any type of container that protects a formulation from being exposed to light (e.g., secondary packaging of a vial). Similarly, any other type of container may be a light-protective container, or packaged within a light-protective container.

The formulations may be administered to a subject, which includes any vertebrate animal, preferably a mammal, and more preferably a human. Examples of subjects include humans, non-human primates, rodents, guinea pigs, rabbits, sheep, pigs, goats, cows, horses, dogs, cats, birds, and fish.

In some embodiments, the 2-IB formulations are suitable for administration to newborn babies and, in particular, to neonates who suffer from, are expected to suffer from, or are otherwise judged to be at risk from, complications during childbirth, in particular, from perinatal asphyxia, which can lead to hypoxia-ischemia. Perinatal asphyxia may also occur well before birth or after and are also suitable for treatment with the 2-IB formulations described herein. The terms "newborn baby" and "neonate" include babies born by natural childbirth as well as babies that have been delivered by, for instance, caesarean section, and also include babies that have been born prematurely and/or the birth of which has been artificially induced.

In some embodiments, the 2-IB formulations are suitable for administration to the mother of the fetus, when an asphyxiated newborn is expected. The term "mother" refers to the mother of the fetus or the newborn baby, including natural, inseminated, induced and carrier mothers.

Usually, treatment of a neonate with the 2-IB formulations will be carried out shortly after childbirth, e.g., during the "window" for therapeutic intervention. Usually, this window spans the first day following childbirth and, in particular, the first 0-24 hours following childbirth. However, if an asphyxiated baby can be expected, treatment may be carried out in the mother before the expected labor, in particular, about 0-24 hours before labor.

As part of such treatment, the 2-IB formulations will generally be administered to the neonates in one or more pharmaceutically effective amounts and, in particular, in one or more amounts that are effective in preventing and/or treating the above-mentioned effects. Such treatment may involve only single administration, but usually—and preferably—involves multiple administrations over several hours or days, e.g., as part of, or according to, an administration regimen or treatment regimen. Such a treatment regimen may, for instance, be as follows: every 4 hours by intravenous injection of the substance during the first 24 hours.

Usually, the amount of 2-IB administered to the neonate will correspond to between 0.01 and 30 mg per kg body weight per day, preferably between 0.1 and 25 mg/kg per day, more preferably between 1.8 and 12 mg/kg/day. These amounts refer to the active component and do not include carrier or adjuvant materials such as carbohydrates, lipids or proteins, or the like. These amounts may be administered as a single dose or as multiple doses per day, or essentially continuously over a certain period of time, e.g., by continuous infusion. Preferably, the 2-IB is administered in 3-6 dosages/day. Preferably, 2-IB is administered to a human neonate in a dose of between 0.01 to 1 mg/kg, preferably between 0.05 to 0.75 mg/kg, more preferably between 0.05 to 0.5 mg/kg. Exemplary doses are 0.075, 0.45, and preferably 0.15 mg/kg.

Treatment may be continued up to 24, 48 or 72 hours after asphyxia, or otherwise until the neonate is judged no longer to be at risk of the effects mentioned above. However, the treatment, especially the preventive treatment, may also involve administration of the 2-IB formulation to the mother before or during parturition. The formulation may be administered to the mother, e.g., orally, subcutaneously, or by intravenous injection. The amounts to be administered can then be the same or higher, depending on the placental transfer and the metabolism, the first pass effect in the liver and the distribution volume of the compound. Thus, the amounts administered to the mother may vary between, e.g., 0.01-25 mg of active component per kg of the body weight of the mother per day.

One aspect of the disclosure provides for treating complications in childbirth comprising the administration of 2-IB in combination with hypothermia. Hypothermia has been demonstrated to have a therapeutic effect in several models of brain injury. For example, numerous publications exist showing the beneficial effect of hypothermia in both in-vitro (M. Onitsuka et al. 1998, mild hypothermia protects rat hippocampal CA1 neurons from irreversible membrane dysfunction induced by experimental ischemia, *Neuroscience Research* 30:1-6) and in-vivo models of neonatal asphyxia (T. Debillon et al. 2003, whole-body cooling after perinatal asphyxia: a pilot study in term neonates, *Developmental Medicine and Child Neurology* 45:17-23).

As used herein, the term "hypothermia" refers to subjecting a particular subject (in this case, a neonatal subject) to hypothermic conditions, for example, by lowering the body temperature through passive or active techniques. Typically, subjecting to hypothermic conditions leads to a decrease in metabolism of body tissues of the subject, thereby decreasing the need for oxygen.

In some embodiments, the core body temperature in a mammal is lowered by at least 1, 2, 3, 4, 5, 6, 7, 8, 9, or 10° below the normal core body temperature for the mammal. In some embodiments, the core body temperature in a mammal is lowered by between 1-10, 2-6, or preferably 2-4° below the normal core body temperature for the mammal.

In one preferred embodiment, the temperature of the mammal is maintained at a temperature of from about 31° to about 37 degrees Celsius. More preferably, the temperature of the mammal is maintained at a temperature of from about 32 degrees Celsius to about 36 degrees Celsius; more preferably from about 32 degrees Celsius to about 35 degrees Celsius; more preferably still from about 33 degrees Celsius to about 35 degrees Celsius.

Induction of hypothermia by lowering of the core temperature of the body may be performed by any method known in the art. Typical hypothermia induction means use either whole body or head cooling. Hypothermia may be induced using ice/cold water or mechanical cooling devices such as surface cooling, the Olympic CoolCap™ system, and cooling using catheters placed in a large vessel. Alternatively, hypothermia may be induced using pharmaceutical agents such as, e.g., vanilloid receptor agonists, capsaicinoids or capsaicinoid-like agonists (described in U.S. Patent Publication 20090197966, the content of which is hereby incorporated by reference) and neurotensin analogs capable of crossing the blood-brain barrier, such as NT69L and NT77 (described in U.S. Pat. No. 7,319,090, the content of which is hereby incorporated by reference).

Hypothermia and 2-IB may be administered simultaneously, sequentially, or separately. As used herein, "simultaneously" is used to mean that the 2-IB is administered concurrently with hypothermia, whereas the term "in combination" is used to mean the 2-IB is administered, if not simultaneously, then "sequentially" within a timeframe in which the 2-IB and the hypothermia both exhibit a therapeutic effect, i.e., they are both available to act therapeutically within the same time-frame. Thus, administration "sequentially" may permit the 2-IB to be administered within 5 minutes, 10 minutes or a matter of hours before or after the hypothermia, provided the circulatory half-life of the 2-IB is such that it is present in a therapeutically effective amount when the neonatal subject is exposed to hypothermic conditions.

In contrast to "in combination" or "sequentially," "separately" is used herein to mean that the gap between administering the 2-IB and exposing the neonatal subject to hypothermia is significant, i.e., the 2-IB may no longer be present in the bloodstream in a therapeutically effective amount when the neonatal subject is exposed to hypothermic conditions.

In one preferred embodiment, the 2-IB is administered in a therapeutically effective amount.

In another preferred embodiment, the 2-IB is administered in a sub-therapeutically effective amount. In other words, the 2-IB is administered in an amount that would be insufficient to produce the desired therapeutic effect if administered in the absence of hypothermic conditions. Even more preferably, the combination of 2-IB and hypothermia has a synergistic effect, i.e., the combination is synergistic.

In some embodiments, the hypothermia is maintained for a period of at least about 6, 12, 18, 24, 36, 48, 72, or 96 hours after the hypoxic-ischemic (HI) insult or after birth. In one preferred embodiment, the hypothermia is maintained for a period of from about 6 to about 24 hours after the hypoxic-ischemic (HI) insult or after birth, preferably at least 72 hours.

Preferably, treatment in accordance with a method hereof is initiated within about 6 hours of the hypoxic-ischemic (HI) insult, and more preferably within about 2 hours, more preferably within 1 hour, of the hypoxic-ischemic insult.

In another aspect, the 2-IB is administered prior to the hypoxic insult. Thus, in one preferred embodiment, the 2-IB is administered to the neonate via the mother prior to birth, for example, by administering to the mother prior to or during labor. Methods are provided for treating neonatal asphyxia in a mammal in need thereof, the method comprising: (a) administering a therapeutically effective amount of 2-IB to the mother of the mammal prior to and/or during labor; and (b) subjecting the mammal to hypothermia after birth.

Preferably, the 2-IB is administered to the mother for up to about 48 or 24 hours prior to birth. After birth, the neonate is then subjected to hypothermic conditions. In some embodiments, 2-IB is administered to the mother as soon as the mother is found at risk or the fetus is found to be asphyctic or has delayed growth.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal), then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

BRIEF DESCRIPTION OF THE DRAWINGS

FIG. 1: Solubility of 2-IB with and without 10% SBE-CD at a different pH.

DETAILED DESCRIPTION

Exemplification

2-IB has both an acidic, carboxylic acid, group as well as a basic amino group. The calculated pKa for these groups are 4.78 for the carboxylic acid group and 11.48 for the amino group, respectively, using the PrologP calculation software. Due to the acidic and basic groups present in 2-IB, 2-IB exhibits zwitterionic behavior in the neutral pH range. As a result, the water solubility of 2-IB is strongly pH dependent and much lower than the calculated value of 35 g/l at neutral pH conditions (see Table 1). Based on the zwitterionic nature of 2-IB, it is difficult to develop a suitable formulation. The following comparative examples demonstrate a number of attempts to develop a formulation of 2-IB suitable for IV administration.

Comparative Example 1

Solvent Selection

Solubility of 2-IB was determined in the following solvents:
0.9% Sodium chloride in water
5% Dextrose in water
N,N-dimethyl acetamide
N,N-dimethylformamide
Dimethyl sulfoxide
Ethanol
Propylene glycol
Polyethylene glycol 400
Corn oil Approximately 10 mg of 2-IB was weighed into a 10 ml tube. Subsequently, small aliquots (100 μl-200 μl-400 μl-800 μl-1600 μl-3200 μl) of the respective solvents were added stepwise. After each addition, the solution was mixed intensively and visually judged for solubility. The end volume for all solvents was 6400 μl (1.6 mg/ml).

In all of the experiments, a large amount of undissolved 2-IB remained after addition of 6400 μl of solvent, indicating that 2-IB is not sufficiently soluble in any of these solvents. After addition of 100 µl of 1 N hydrochloric acid, 2-IB fully dissolved in all solvents. This further illustrates the zwitterionic behavior of 2-IB and the strong influence of pH on solubility.

Visually, the highest fraction of 2-IB was dissolved in propylene glycol. Therefore, the experiment was repeated for propylene glycol but with addition of 100 µl N hydrochloric acid after 200 µl propylene glycol (i.e., 10 mg 2-IB+200 µl propylene glycol+100 µl 1 N hydrochloric acid). This resulted in a 33 mg/ml solution of 2-IB that was fully dissolved and stable. Addition of water to this formulation immediately resulted in precipitation of 2-IB illustrating that this is not a viable route toward an IV formulation.

Since all solvents tested required the addition of acid for full solubilization of 2-IB, it was decided to continue with 5% dextrose in water since the other solvents were obviously much less biocompatible during IV introduction or possessed a higher risk of salting out effects (0.9% sodium chloride in water).

When an acidified 2-IB formulation in 5% dextrose is prepared, the pH after acidification is approximately 2 for nominal 2-IB concentrations in the range 1-5 mg/ml. Partial neutralization with 0.1% sodium hydroxide is possible up to a pH of 3-3.5 (depending on nominal concentration) but eventually precipitation of 2-IB occurs, first in the form of very fine "hair"-like needles that grow out to larger agglomerates. At a pH of 7, nearly all 2-IB has precipitated out of solution based on visual observation.

Comparative Example 2

Surfactants

The following surfactants were studied for their solubility-enhancing behavior:

Hexadecyl trimethyl ammonium bromide (cationic surfactant, 1%)

Polyoxyethylene(40) stearate (non-ionic surfactant, 1%, 0.1% and 0.01%)

Polysorbate 80 (non-ionic surfactant, 1%)

Sodium dodecylsulfate (anionic surfactant, 1%, 0.1%, 0.01%)

Stock solutions of the surfactant were prepared in 5% dextrose. The test procedure used was the stepwise addition of the respective surfactant solution to a small amount of 2-IB (10 mg), as described in Comparative Example 1. 2-IB did not dissolve in any of the surfactant solutions at the nominal concentration of 1.6 mg/ml without the addition of acid. After addition of acid, it fully dissolved, but following subsequent (partial) neutralization with 0.1 N sodium hydroxide, 2-IB precipitated again exactly as was observed in the experiments without surfactants. This leads to the conclusion that the surfactants do not enhance the solubility of 2-IB (also not at low pH) and are, therefore, not a useful addition for formulations.

Table 1 depicts several examples of 2-IB solubility in various formulations. An excess of 2-IB was added to the solvent/surfactant solutions, mixed at room temperature and then filtered to removed non-solubilized 2-IB. These solutions were then analyzed by RP-HPLC to determine the solubilized content of 2-IB.

TABLE 1

Overview of 2-IB

| Description | Visual inspection after 12 hours at 5° C. | Conc. 2IB (mg/mL) |
|---|---|---|
| 2-IB in 10% Propylene glycol/90% water | Precipitation | 0.40 |
| 2-IB in 30% Propylene glycol/70% water | Small amount of precipitation | 0.51 |
| 2-IB in 10% PEG 300/90% water | Small amount of precipitation | 0.35 |
| 2-IB in 30% PEG 300/70% water | No precipitation | 0.38 |
| 2-IB in 2% TWEEN ® BO/98% water | No precipitation | 0.37 |
| 2-IB in 10% CREMOPHOR ® ELP/90% water | No precipitation | 0.34 |
| 2-IB in 10% Propylene glycol, 10% PEG 300/80% Water | Small amount of precipitation | 0.24 |
| 2-IB in 10% Propylene glycol, 10% PEG 300, 2% TWEEN ® 80/78% Water | Small amount of precipitation | 0.37 |
| 2-IB in 10% Propylene glycol, 10% PEG 300, 10% CREMOPHOR ® ELP/70% Waier | Small amount of precipitation | 0.35 |
| 2-IB in 10% Propylene glycol, 10% PEG 300, 2% TWEEN ® 80, 10% CREMOPHOR ® ELP/68% Water | Small amount of precipitation | 0.33 |

Comparative Example 3

Cyclodextrins

The following cyclodextrins were tested, all at a 1% concentration in a 5% dextrose solution:

α-cyclodextrin

β-cyclodextrin hydroxypropyl-α-cyclodextrin (2-hydroxypropyl)-β-cyclodextrin (2-hydroxypropyl)-γ-cyclodextrin Similar to the surfactants, no increase in solubility was observed during any of the experiments, also not at low pH.

Comparative Example 4

Novel Excipients

Finally, two novel excipients were tested, CREMOPHOR® EL and SOLUTOL® HS 15. Stock solutions of these excipients were prepared at a concentration of 10% in 5% dextrose and then the stepwise solubility approach was performed. Using SOLUTOL® HS 15, the best results were obtained (after addition of hydrochloric acid) and, therefore, the next step was to optimize the SOLUTOL® HS 15 concentration.

Five concentrations, 5-10-15-20-25%, of SOLUTOL® HS 15 were tested at a formulation concentration of approximately 5 mg/ml (Table 2). Optimal solubility of 2-IB was observed in 20% SOLUTOL® HS 15, but still a very acidic (pH<2) initial solution was required to solubilize 2-IB complete. However, upon subsequent partial neutralization with sodium hydroxide precipitation of 2-IB occurred at higher pH and at much lower amounts than that observed in formulations of 2-IB in dextrose. A range of 2-IB formulations were prepared that were stored for 48 hours and measured for 2-IB content:

TABLE 2

| Nominal concentration (mg/ml) | pH[1] | Concentration t = 0 (mg/ml)[2] | Concentration t = 48 hours (mg/ml)[2] | Concentration t = 48 hours relative to t = 0 (%)[2] |
|---|---|---|---|---|
| 5.0 | 2.4 | 5.65 | 4.78 | 85 |
|  | 2.8 | 5.43 | 5.45 | 100 |
|  | 3.0 | 4.64 | 4.87 | 105 |
|  | 3.5 | 5.21 | 4.94 | 95 |
|  | 3.6 | 4.52 | 3.93 | 87 |
|  | 3.8 | 5.10 | 2.62 | 51 |
|  | 10.2 | 5.71 | 0 | 0 |
| 10 | 3.0 | 9.06 | 8.64 | 95 |
|  | 3.5 | 8.30 | 8.04 | 97 |
| 20 | 3.0 | 16.6 | 16.7 | 101 |
|  | 3.5 | 14.7 | 13.2 | 90 |

[1]pH adjusted using 1N hydrochloric acid and 0.1N Sodium hydroxide
[2]Concentration was analyzed after filtration Based on the research performed during this project, a vehicle consisting of 20% SOLUTOL® HS 15 and 5% Dextrose in water was selected as the optimal vehicle for preparation of 2-IB formulations. Due to the zwitterionic nature of 2-IB, the formulation could only be prepared at a relatively low pH (i.e., <3.5-3.6).

Comparative Example 5

SOLUTOL® HS 15 Toxicity Study

Preliminary toxicity study via continuous intravenous infusion in Wistar rats.

Group I: vehicle 20% SOLUTOL® (continuous intravenous infusion)

Animals received a continuous infusion of vehicle only (20% SOLUTOL® in 5% dextrose) at a dose volume of 4 mL/kg/hour for 24 hours.

No mortality occurred and body weights were normal. A hunched posture and piloerection was noted for all animals from approximately 12 hours after start of infusion onward. Necropsy was performed to investigate any macroscopic effects of SOLUTOL® treatment. Macroscopic findings at necropsy comprised of yellow discoloration of the whole body and body cavities (2/4), minimal fibrin-like coating in the vena cava (4/4), accentuated lobular pattern of the liver (1/4), a small liver (1/4), and pelvic dilation of the kidneys (1/4).

Group II: vehicle 5% SOLUTOL® (Continuous Intravenous Infusion)

Animals received a continuous infusion of vehicle only (5% SOLUTOL® in 5% dextrose) at a dose volume of 4 mL/kg/hour for approximately 96 hours.

No mortality occurred, no consistent clinical signs were observed, and body weights were normal. A moderate to marked increase in alanine aminotransferase (2/3), aspartate aminotransferase (2/3) and bilirubin (2/3), and a slight increase in alkaline phosphatase (3/3) and glucose (3/3) was found at the end of treatment. Yellow discoloration of plasma was observed for two animals.

Group III: 960 mg/kg/24 hours of 2-IB in 5% SOLUTOL® (continuous intravenous infusion).

Animals received a continuous infusion (dose concentration of 10 mg/mL at a dose volume of 4 mL/kg/hour) using 5% SOLUTOL®/5% dextrose (the end concentration of dextrose and saline was hypotonic; approximately 2.5% and 0.45%, respectively). The infusion was terminated after 46 hours, due to adverse clinical effects and difficulties with the formulation in the infusion system (pump alarms indicative of blockage of the infusion systems, probably at the swivels).

One animal died after 46 hours of infusion. Body weights were increased for two animals. A hunched posture, piloerection and pallor were observed for all animals on Days 2-3 of treatment. A slight to moderate increase in aspartate aminotransferase (1/2), alkaline phosphatase (1/2), and glucose (2/2) was found at the end of treatment, as well as high values for creatinine and urine (1/2). Bilirubin levels were within the normal range.

Macroscopic findings at necropsy comprised of edema (2/3), pelvic dilation of the kidneys (2/3), enlarged liver (1/3), enlarged iliac lymph node (1/3), dark spots on the lungs (1/3), and fibrin-like coating in or around the femoral vein. Yellow discoloration of tissues was not in evidence.

Based on these results, it was concluded that, although better dissolution characteristics in 5-20% SOLUTOL® were found for 2-IB, this vehicle was not suitable for continuous intravenous infusion in rats with the applied dose volumes and rates.

Comparative Example 6 pH

The solubility of 2-IB (5 mg/ml) was tested using different acids. The solubility was achieved at a relatively higher pH (pH 3.3) using weak acids (acetic acid and citric acid) in comparison to pH 3.0 using HCl. This difference is probably due to the synergistic effect of pH-adjustment and the hydrogen-bonding formation between 2-IB and the carboxylic groups of weak acids.

Comparative Example 7

Citrate Buffer

An excess of 2-IB was added to citrate buffers, mixed at room temperature, and then filtered to remove non-solubilized 2-IB. These solutions were then analyzed by RP-HPLC to determine the solubilized content of 2-IB (Table 3). The solubility of 2-IB in 50 mM citrate buffer at a range of pH was determined to be 11 mg/ml at pH 3.0 (room temperature). At pH 3.5, there is approximately half the amount of 2-IB solubilized.

TABLE 3

| pH of 50 mM Citrate | Final pH | Final Citrate (mM) | Appearance after 12 hours at 5° C. | Conc. 2-IB (mg/mL) |
|---|---|---|---|---|
| 3.0 | 3.07 | 106 | Precipitated | 11.27 |
| 3.5 | 3.52 | 65 | Precipitated | 4.45 |
| 4.0 | 4.03 | 52 | Precipitated | 1.72 |
| 4.5 | 4.54 | 49 | Precipitated | 0.86 |
| 5.0 | 5.02 | 49 | Precipitated | 0.59 |

Example 1

Although the earlier experiments demonstrated that cyclodextrin did not significantly increase 2-IB solubility, the experiments were repeated using higher concentrations of cyclodextrin. Surprisingly, in contrast to the results from using 1% cyclodextrin, it was found that a higher concentration of cyclodextrin did increase 2-IB solubility. An excess of 2-IB was added to the cyclodextrin solutions, mixed at room temperature for three days and then filtered to remove non-encapsulated/non-solubilized 2-IB. These solutions were then analyzed by RP-HPLC to determine the solubilized content of 2-IB (see Table 13). Approximately 14 mg/ml of 2-IB was dissolved/encapsulated in 40% SBE-CD in 50 mM Citrate pH 4.0 with a final formulation pH of 5.1. At 40% SBE-CD but using Citrate buffer pH 5 with a final pH of 5.5, approximately 10 mg/ml was encapsulated. At 40% SBE-CD, but using water with a final pH of 6.8, approximately 4.2 mg/ml was dissolved/encapsulated. The results of this experiment demonstrate that suitable levels of 2-IB can be encapsulated using a combination of relatively low pH, a low starting pH, and a 5-20% cyclodextrin concentration.

The results indicate a clear difference with the encapsulation efficiency of 2-IB for two types of cyclodextrin used. The solubility of 2-IB in SBE-CD (Sulfobutylether-β-cyclodextrin) with water shows that at 40% SBE-CD, 4.2 mg/ml 2-IB is encapsulated. This is significantly higher than the 1.2 mg/ml 2-IB that was encapsulated using 40% HP-CD (Hydroxypropyl-β-cyclodextrin). The higher solubility of 2-IB in SBE-CD than in HP-CD could not be only attributed to the inclusion complexation by encapsulation because Mw of SBE-CD (2163) is higher than HP-CD (1400). Other physical interactions between 2-IB and SBE-CD molecules might contribute to the higher solubility, such as hydrogen bonding or charge interaction.

Visual inspection of the cyclodextrin formulations after 12 hours' storage at 5° C. showed that both formulation pH and the concentration of cyclodextrin has an effect on the stability of the formulation in terms of precipitation/release from encapsulation (Table 13). For the SBE-CD formulations, all formulations remained encapsulated (clear solution) except the formulation with the lowest cyclodextrin concentration or 2.5% at pH 4.4. At a higher concentration of cyclodextrin (5%) with a comparable pH (4.5), the 2-IB remained solubilized. Similarly, at a comparable cyclodextrin concentration (2.5%) but a higher pH (5.0), the 2-IB remained solubilized, indicating that both pH and cyclodextrin concentration contribute to the stability of the SBE-CD formulations during storage at pH 5. Tables 4A and 4B summarize the effects of pH and cyclodextrin type and concentration on 2-IB.

TABLE 4A

Effect of SBE-CD and pH on the concentration of 2-IB (mg/ml)

| | SBE-CD | | | | | |
|---|---|---|---|---|---|---|
| | WFI | | Citrate pH 5.0 | | Citrate pH 4.0 | |
| % Cyclodextrin | Final pH | 2-IB mg/ml | Final pH | 2-IB mg/ml | Final pH | 2-IB mg/ml |
| 0 | 6.5 | 0.4 | 5.0 | 0.6 | 4.0 | 1.7 |
| 2.5 | 6.3 | 0.7 | 5.0 | 1.9 | 4.3 | 3.7 |
| 5 | 6.5 | 1.0 | 5.1 | 2.9 | 4.4 | 5.5 |
| 10 | 6.5 | 1.5 | 5.1 | 4.6 | 4.6 | 8.0 |
| 20 | 6.7 | 2.4 | 5.3 | 7.0 | 4.9 | 11.4 |
| 40 | 6.8 | 4.2 | 5.5 | 9.9 | 5.1 | 14.5 |

TABLE 4B

Effect of HP-CD and pH on the concentration of 2-IB (mg/ml)

| | HP-CD | | | | | |
|---|---|---|---|---|---|---|
| | WFI | | Citrate pH 5.0 | | Citrate pH 4.0 | |
| % Cyclodextrin | Final pH | 2-IB mg/ml | Final pH | 2-IB mg/ml | Final pH | 2-IB mg/ml |
| 0 | 6.5 | 0.4 | 5.0 | 0.6 | 4.0 | 1.7 |
| 2.5 | 6.5 | 0.5 | 5.1 | 0.9 | 4.2 | 2.5 |
| 5 | 6.5 | 0.5 | 5.1 | 1.2 | 4.3 | 3.0 |
| 10 | 6.5 | 0.6 | 5.2 | 1.6 | 4.5 | 4.1 |
| 20 | 6.6 | 0.9 | 5.3 | 2.1 | 4.7 | 5.1 |
| 40 | 6.7 | 1.2 | 5.6 | 2.6 | 5.0 | 5.6 |

Example 2

The solubility of 2-IB was screened in 10% SBE-CD solutions at different pH adjusted with 0.1 M citric acid solution. The experimental steps are shown below.
1. Weigh 0.5 g of SBE-CD into 10 ml glass vial
2. Add 3 ml WFI into each vial to dissolve SBE-CD
3. Weigh excess amount of 2-IB (25 mg-100 mg) into different vials
4. Magnetic stirring for 1 hour
5. Adjust pH to target pH with 0.1 M citric acid
6. Determine the weight of 0.1 M citric acid added
7. Add WFI to total weight of 5 g
8. Measure pH again after 1 hour stirring
9. Filtrate through the formulation through PVDF 0.22 µm filter
10. Determine the solubility of 2-IB by HPLC method The solubility of 2-IB increased from 1.71 mg/g to 13.08 mg/g with pH decrease from 7.0 to 4.0 (Table 5). The saturated solutions were physically stable and no precipitates were observed at room temperature. However, 2-IB precipitates were observed after 5 days' storage at 5 degrees C. (Table 5). In the presence of 10% SBE-CD, the solubility of 2-IB was significantly increased when compared to pH-adjustment alone (pH 5.0: 5.2 vs. 0.59 mg/g; pH 4.0: 13.08 vs. 1.72 mg/g). The solubility increased 7.6-8.8 times in the presence of 10% SBE-CD (FIG. 1).

TABLE 5

Solubility of 2-IB in 10% SBE-CD at different pH

| SBE-CD, % | pH | Solubility of 2-IB, mg/g | 5 days at 5° C. | 5 days at RT |
|---|---|---|---|---|
| 10 | 7.0 | 1.71 | − | + |
| 10 | 6.2 | 1.94 | − | + |
| 10 | 5.5 | 3.29 | − | + |
| 10 | 5.0 | 5.21 | − | + |
| 10 | 5.1 | 5.30 | − | + |
| 10 | 4.5 | 9.00 | − | + |
| 10 | 4.0 | 13.08 | − | + |

−: Precipitation of 2-IB;
+: no precipitation

Example 3

Six formulations were prepared containing 8-10% of SBE-CD (Table 6A). The concentration of 2-IB in each formulation was approximately 75% of 2-IB solubility to prevent the precipitation of 2-IB at low temperature (Table 6A vs. Table 5). The final pH was adjusted with 0.1 M citric acid solution (or 0.1 M sodium citrate) to pH 4.0-6.0. The detailed procedure of formulation preparation is described as below using F429-02-001P004 as an example (see Table 14).

F429-02-001p004: 3.9 mg/g 2-IB, 10% SBE-CD, pH 5.0
1. Add 82.93 g water for injection in 200 ml glass bottle
2. Weigh 10 g of SBE-CD powder into the glass bottle and to be dissolved under magnetic stirring
3. Weigh 400 mg of 2-IB
4. Add 6.67 g of 0.1 mM citric acid solution
5. Magnetic stir 5 minutes to completely dissolve 2-IB
6. Adjust pH to 5.0 with 0.1 M sodium citrate
7. Filtrate the solution through 0.22 µm filter (Millex-GP (PES))
8. Fill 1.5 ml in 6 ml glass vial and store at 5, 25, and 40° C.

TABLE 6A

Formulations of 2-IB based on SBE-CD at different pH

| SBE-CD, % | Citric add, mM | Sodium citrate, mM | 2-IB, mg/g | pH |
|---|---|---|---|---|
| 10 | 0.6 | 0.0 | 1.5 | 6.0 |
| 10 | 2.0 | 0.0 | 2.5 | 5.5 |
| 10 | 6.6 | 1.5 | 3.9 | 5.0 |
| 8 | 5.6 | 0.0 | 4.0 | 5.0 |
| 10 | 15.0 | 0.2 | 7.0 | 4.5 |
| 10 | 32.3 | 3.5 | 9.7 | 4.0 |

Although the solubility of 2-IB at pH 7.0 is 1.71 mg/g, a formulation at pH 7.0 with 1.5 mg/g of 2-IB in water was tested and was not feasible because 2-IB did not dissolve completely after overnight stirring. This might be due to the different approaches for the solubility testing and the formulation preparation. For the solubility testing, an excess amount of 2-IB powder was added in 10% SBE-CD solution and the small particles of 2-IB might dissolve quickly to reach the equilibrium. However, a precise amount of 2-IB powder was added for the formulation preparation, which contains 2-IB particles with different sizes. The large size of 2-IB particles might have a very slow dissolution rate in water at pH 7.0. For the six formulations in Table 6A, 2-IB was quickly dissolved within 30 minutes, indicating a fast dissolution rate. The six formulations were all transparent and colorless solutions.

It is not feasible to increase the solubility by preparing a formulation at a low pH first and then titrate to a high pH. Precipitation was observed when titrating the formulation F429-02-001P004 from pH 5.0 to pH 5.9 and the formulation F429-02-001P006 from pH 4.0 to pH 5.1 with 0.1 M tri-sodium citrate.

The six formulations in Table 6A were stored at 5, 25, and 40° C. for six weeks. At the time-point of T=0, 2 weeks, 4 weeks, and 6 weeks, the formulations were tested for appearance, pH, osmolality, and purity and content of 2-IB (HPLC) (Table 15). After 6 weeks storage, no precipitation was observed in the formulations at three storage conditions (Table 16). The appearance of the six formulations did not change at 5 and 25° C. by visual inspection. However, a slight brownish color was observed at 40° C. The color intensity appeared to increase with the increase of 2-IB concentration and the decrease of pH. The reason for this is not known. It appears that 2-iminobiotin is stable and the purity and content did not change. SBE-CD only degraded at extreme low pH and high temperature. pH and osmolality of the six formulations remain stable after 2, 4, and 6 weeks' storage at 5, 25, and 40° C. compared to T=0 values.

2-IB remains stable in the six formulations after 6 weeks' storage at 5, 25 and 40° C. based on the purity, content, and recovery (Table 17). The purity of 2-IB in the six formulations was calculated based on the % peak area of 2-IB measured by the HPLC method. It was approximately 99% and did not decrease after 6 weeks' storage at 5, 25 and 40° C. The reason for the slightly higher content and the recovery compared to T=0 was likely due to the analytical variation of the HPLC method.

Example 4

Formulation conditions were further studied as shown in Tables 18 and 19. Each formulation was prepared to a final volume of 10 ml. 2-IB was weighed for the formulation preparation, taking into account water content as specified in the CoA of this batch (4.2% w/w). The preliminary stability of the formulations was evaluated by visual inspection for 3 days' storage at 5, 25 and 40° C. At T-0, samples were characterized additionally for pH and osmolality.

Example 5

Two of the formulations from Example 4 were studied in more detail. Formulations F30 and F34 were prepared as follows. 2-IB was weighed into a pre-weighted glass bottle, taking into account water content (4.2% w/w). Citric acid 100 mM (90% from total amount), NaCl/SBE-CD stock solution and WFI (water for injection) (80% from total amount) was added. The mixture was stirred using a magnetic stirrer plate. pH was above 4.0 and adjusted to 4.0±0.2 using Citric acid 100 mM solution. Final weight of the solution was corrected by addition of WFI to obtain 750 g. The obtained formulation was filtered using MILLIPAK® 20 DURAPORE® (PVDF membrane). Both formulations were divided to nine ethylene vinyl acetate infusion bags containing approximately 70 ml of solution. The composition of the formulation is shown in Table 6B.

TABLE 6B

|  | F30 (g) | F34 (g) |
| --- | --- | --- |
| 2-IB (95.8%) | 0.418 | 0.522 |
| NaCl | 0.490 | 0.490 |
| SBE-CD | 5.00 | 5.00 |
| Citric acid (100 mM) | 11.7 | 14.3 |
| WFI | Up to 100 g | Up to 100 g |

A sample of both formulations was tested for appearance, pH, osmolality, 2-IB content and purity immediately after preparation. Samples for stability were stored at three temperatures: 5° C., 25° C. and 40° C. Time points for the stability were 1 day, 2 days and 3 days. At each stability time point, 2-IB samples at all storage conditions were tested for appearance, pH, 2-IB content and purity. Both tested formulations were found to be stable for 3 days at 5° C., 25° C. and 40° C. (see Tables 19A and 19B).

Example 6

The two formulations from Example 4 were tested to predict their potential for precipitation upon injection based on the In-Vitro Static Serial Dilution Model described in article of P. Li, R. Vshnuvajjala, S. E. Tabibi, and S. H. Yalkovsky, "Evaluation of in-vitro precipitation methods" published in *J. Pharma. Sci.* 1998 February; 87(2):196-9.

The procedure was performed as follows:
Three ml of formulation were diluted with 3 ml of ISPB or vehicle and agitated. (Isotonic Sorensen Phosphate buffer (ISPB) pH 7.4 was prepared using sodium phosphate dibasic heptahydrate—2.146%, sodium dihydrogen phosphate dehydrate—0.296% and sodium chloride—0.178%). Three ml of the resulting solution/suspension were then mixed with another 3 ml of ISPB/vehicle. This step was repeated until seven serial dilutions were obtained. In addition, a control tube for each dilution was prepared using vehicle as a diluent instead of ISPB.

Visual observations were used to determine the presence or absence of precipitate upon mixing. Following this initial observation, the formulation-buffer mixtures were placed in a water bath at 37° C. and 50 rpm for 1 hour and then centrifuged. The upper phase was analyzed by HPLC method.

For purposes of data analysis, the formulation-diluent ratio is defined as the ratio of the volume of formulation to the total volume (volume of formulation+volume of ISPB). The difference between the control concentration and the measured concentration in each dilution is the amount of drug absent per ml of original formulation.

In-vitro static serial dilution model for formulation F30

Formulation F30 was tested to predict its potential for precipitation upon injection using the in-vitro static serial dilution model. In this method, the formulation was sequentially diluted in a one-to-one ratio with ISPB. The appearance of the formulation at the different dilution steps is presented in Table 7. The equilibrium concentration of 2-IB obtained at each dilution step and the amount of drug absent per ml are presented in Table 8 (n=3 for each dilution). The equilibrium concentration in each diluted solution was determined by HPLC method. The difference between the control concentration and the measured concentration in each dilution is equal to the amount of drug that precipitated from 1 ml of original formulation. The formulation-diluent ratio is defined as the ratio of the volume of formulation to the total volume. At formulation-diluent ratio of 0.5, the formulation turned to translucent and slight precipitation was observed upon standing. The amount of drug lost at these dilution ratios was slight, and is probably a result of precipitation of the drug. Formulation-diluent ratios of 0.25-0.0625 resulted in a clear solution but the analytical results demonstrated that drug was lost. The missing drug amount may be a result of tiny precipitation, which was not observed visually or adsorption of the drug to the tube wall.

TABLE 7

Visual observation of serial dilution steps

| Dilution no. | Formulation-diluent ratio | Appearance after preparation | Appearance after incubation |
| --- | --- | --- | --- |
| 1 | 0.5 | Clear solution | Translucent solution with slight precipitation |
| 2 | 0.25 | Clear solution | Clear solution |
| 3 | 0.125 | Clear solution | Clear solution |
| 4 | 0.0625 | Clear solution | Clear solution |
| 5 | 0.03125 | Clear solution | Clear solution |
| 6 | 0.015625 | Clear solution | Clear solution |
| 7 | 0.007875 | Clear solution | Clear solution |

TABLE 8

Mean equilibrium 2-IB concentrations and amount of 2-IB absented per ml for the different formulation-diluent ratios (average of n = 3)

| Formulation-diluent ratio | Control 2-IB concentration (mg/ml) | Mean equilibrium 2-IB concentration (mg/ml) | 2-IB absent (mg/ml) |
| --- | --- | --- | --- |
| 1 | 4.188 | 4.188 | 0.000 |
| 0.5 | 2.074 | 2.066 | 0.048 |
| 0.25 | 1.039 | 1.025 | 0.031 |
| 0.125 | 0.526 | 0.511 | 0.015 |
| 0.0625 | 0.265 | 0.256 | 0.009 |
| 0.03125 | 0.128 | 0.127 | 0.000 |
| 0.015625 | 0.063 | 0.064 | 0.000 |
| 0.007875 | 0.030 | 0.032 | 0.000 |

In-vitro static serial dilution model for formulation F34

Formulation F34 was tested to predict its potential for precipitation upon injection using the in-vitro static serial dilution model. The appearance of the formulation at the different dilution steps is presented in Table 9. The equilibrium concentration of 2-IB obtained at each dilution step and the amount of drug absent per ml are averaged in Table 10. At formulation-diluent ratios of 0.5-0.125, the formulation turned to turbid-to-translucent and precipitation was observed. The amount of drug lost at these dilution ratios was perceptible, and is probably a result of precipitation of the drug. As dilution continues and ratio reached 0.0625, a precipitate was observed but not detected by analytical test, probably due to a minor amount of a precipitate. Below the ratio 0.0625, the equilibrium concentration points overlap the control curve with the observation that the precipitate is redissolved.

TABLE 9

Visual observation of serial dilution steps

| Dilution no. | Formulation-diluent ratio | Appearance after preparation | Appearance after incubation |
|---|---|---|---|
| 1 | 0.5 | Turbid solution with pronounced precipitation | Turbid solution with pronounced precipitation |
| 2 | 0.25 | Turbid solution with precipitation | Turbid solution with precipitation |
| 3 | 0.125 | Translucent solution with slight precipitation | Translucent solution with slight precipitation |
| 4 | 0.0625 | Clear solution with slight precipitation | Clear solution with slight precipitation |
| 5 | 0.03125 | Clear solution | Clear solution |
| 6 | 0.015625 | Clear solution | Clear solution |
| 7 | 0.007875 | Clear solution | Clear solution |

TABLE 10

Mean equilibrium 2-IB concentrations and amount of 2-IB absented per ml for the different formulation-diluent ratios (n = 3 for each dilution)

| Formulation-diluent ratio | Control 2-IB concentration (mg/ml) | Mean equilibrium 2-IB concentration (mg/ml) | 2-IB absent (mg/ml) |
|---|---|---|---|
| 1 | 5.12 | 5.12 | 0.000 |
| 0.5 | 2.565 | 0.929 | 1.636 |
| 0.25 | 1.263 | 0.697 | 0.565 |
| 0.125 | 0.632 | 0.433 | 0.199 |
| 0.0625 | 0.317 | 0.358 | 0.000 |
| 0.03125 | 0.158 | 0.184 | 0.000 |
| 0.015625 | 0.078 | 0.091 | 0.000 |
| 0.007875 | 0.038 | 0.046 | 0.000 |

For the 4 mg/ml F30 formulation, the results showed no cloudiness or precipitation following serial dilution and the expected 2-IB concentrations were found, indicating that 2-iminobiotin (4 mg/ml) SBE-CD-based formulation is unlikely to precipitate in vivo due to physiological dilution by blood flow upon intravenous administration.

Example 7

The nature and purpose of this study was to assess the placental transfer of 2-iminobiotin (2-IB) and possible passage of 2-IB over the blood-brain-barrier, when administered by two subcutaneous injections to female Wistar rats on Day 20 post-coitum.

Four female Wistar rats were subcutaneously injected on Day 20 post-coitum with 55 mg/kg of 2-IB (each injection of 27.5 mg/kg). The 2-IB was prepared in a physiological saline solution, pH 3.6-3.8, with a concentration of 2.75 mg/ml. No mortality occurred amongst material animals during the study period and all fetuses were viable. Necropsy took place approximately one hour after the second injection. Blood and brain samples were collected from both the mother and fetuses.

2-IB was quantifiable in the plasma samples of all maternal animals and fetuses. Plasma 2-IB concentrations were 3-7 times higher for the maternal animals (average concentration was 10,039 ng/mL) than for their fetuses (average concentration was 1,765 ng/mL for the males and 1,903 ng/mL for the females).

TABLE 11A

2-IB plasma concentration

| | Concentration maternal animals (ng/mL) | Concentration pooled fetuses male (ng/mL) | Concentration pooled fetuses female (ng/mL) |
|---|---|---|---|
| female 1 | 7,104 | 1,868 (n = 8) | 2,442* (n = 3) |
| female 2 | 14,185 | 2,080 (n = 4) | 2,063 (n = 8) |
| female 3 | 7,490 | 1,598 (n = 5) | 1,474 (n = 4) |
| female 4 | 11,378 | 1,512 (n = 8) | 1,634 (n = 7) |
| average (±SD) | 10,039 (±3371) | 1,765 (±259) | 1,903 (±437) |

Lower Limit of Quantification (LLOQ) was 5.0 ng/mL and Upper Limit of Quantification (ULOQ) was 5000 ng/mL.
*Indicative value (initial analytical batch was rejected, but due to the low volume, this sample could not be re-analyzed).
2-IB was quantifiable in the brain samples of all maternal animals and fetuses. Brain 2-IB concentrations were comparable in maternal animals (average concentration was 268 ng/g) and their fetuses (average concentration was 329 ng/g for the males and 369 ng/g for the females).

TABLE 11B

2-IB concentration in brain sample

| | Concentration maternal animals (ng/g) | Concentration pooled fetuses male (ng/g) | Concentration pooled fetuses female (ng/g) |
|---|---|---|---|
| female 1 | 151 | 287 (n = 8) | 474 (n = 3) |
| female 2 | 375 | 435 (n = 4) | 317 (n = 8) |
| female 3 | 270 | 283 (n = 5) | 329 (n = 4) |
| female 4 | 276 | 309 (n = 8) | 356 (n = 7) |
| average (±SD) | 268 (±92) | 329 (±72) | 369 (±72) |

LLOQ was 20.0 ng/g and ULOQ was 5000 ng/g.

In general, 2-IB passage to the brain appeared to be relatively lower in maternal animals (average brain-to-plasma ratio was 0.03, ranging from 0.02 to 0.04) than in their fetuses (average brain-to-plasma ratio was 0.19, ranging from 0.15 to 0.21 for the males and 0.20, ranging from 0.15 to 0.22 for the females).

Bioanalytical results showed that all maternal animals and their fetuses were exposed to 2-IB after subcutaneous injections, with maternal animals showing 3-7 times higher plasma concentrations than their fetuses (average plasma 2-IB concentration was 10,039 ng/mL for maternal animals, and 1,765 ng/mL for the male and 1,903 ng/mL for the female fetuses). In addition, 2-IB concentrations could be measured in the brains of all maternal animals (average concentration was 268 ng/g) and their fetuses (average concentration was 329 ng/g for the male and 369 ng/g for the female fetuses). 2-IB passage to the brain appeared to be relatively lower in maternal animals (average brain-to-plasma ratio was 0.03) than in their fetuses (average brain-to-plasma ratio was 0.20). Based on the above-mentioned results, transfer of 2-IB over the placenta and the blood-brain barrier is confirmed after two subcutaneous injections in Wistar rats at a total dose level of 55 mg/kg.

Example 8

Solutions of 2-IB at the concentrations 0.6 mg/g, 0.75 mg/g and 1 mg/g in citrate buffers at a pH of 3.8, 4.0 and 4.2, respectively, were prepared to a final weight of 20 g as follows (buffer capacity target at pH 4.0 was 15 mM):

A citric acid 0.1 M solution and a sodium citrate dihydrate 0.1 M solution were each prepared in WFI. Citric acid solution was added to 2-IB weighed into a pre-weighed glass vial (taking into account water content as specified in the CoA of this batch (4.2% w/w)). WFI was added for dilution, and then sodium citrate dihydrate 0.1 M solution was added to adjust pH up to the required pH value. WFI was added up to a total weight of 20 g followed by pH measurement.

The 12 bulk solutions obtained were subsequently divided and stored in stability chambers at 5° C.±3° C. and 25° C.±2° C. for 3 days. All stored solutions were evaluated for pH and appearance at each time point (0, 1, 2, 3 days).

Table 20 shows the composition of the citric acid buffer formulations, and the intended and measured pHs before and after addition of WFI to a total formulation weight of 20 g.

Example 9

In a subsequent study, the stability of 2-IB citrate buffer solution formulations at pH 4±0.2 at a temperature at 15° C.±3° C. and 25° C.±2° C. was examined. 24B-citrate buffer formulations at 2-IB concentrations of 0 mg/ml (placebo), 0.75 mg/ml and 1 mg/ml in citrate buffer pH 3.8, 4.0 and 4.2 were prepared as described in Example 8. Each formulation was prepared to a final weight of 20 g (buffer capacity target was 15 mM at pH 4.0), and each was visually examined for appearance and pH determined. The solutions were divided and stored in stability chambers at 15° C.±3° C. and 25° C.±2° C. for 3 days. All stored solutions were evaluated for pH and appearance at time points T=0, 1, 2, and 3 days.

Table 21 presents the composition of each of the citric acid buffer foundations, and the intended and measured pH values before and after addition of WFI to a total formulation weight of 20 g. Appearance and pH data for each of the time points are presented as well.

Example 10

The solubility of 2-iminobiotin was assessed in a buffered 5% CAPTISOL® solution for pH values of 4.0-6.2. The formulations also included NaCl for adjustment of osmolality, and the citrate buffer concentration aimed for at pH 4.0 was 15 mM. The 2-IB concentrations of these solutions were 4.0, 2.0, 1.0, 0.75, and 0 mg/g (placebo) 2-IB.

Preparation of a citric acid 0.1 M solution and the citrate dihydrate 0.1 M solution is described in Example 8. A bulk solution of 25% CAPTISOL®—2.45% NaCl solution was prepared and used for further preparation of the formulations.

Each of the final bulk formulations was visually examined for appearance and pH determined. The solutions were divided and stored in stability chambers at 5° C.±3° C. and 25° C.±2° C. for 3 days. All stored solutions were evaluated for pH and appearance at time points T=0, 1, 2, and 3 days.

Tables 22 and 23 present the composition of the 2-IB citrate buffer solutions and the appearance and pH data.

Example 11

A short-term stability (STS) study of 2-IB in citrate buffer was performed (timepoints: T=0, 2 weeks, 4 weeks, and 6 weeks) on the following formulations:

Formulation 03-15 comprising: 0.75 mg/g 2-IB in citrate buffer pH 6.0, with 5% CAPTISOL® and 2.45% NaCl (for isotonicity) solution and Formulation 02-5B comprising: 0.75 mg/g 2-IB in citrate buffer pH 4.0, with NaCl for isotonicity.

The following parameters were studied: visual appearance, pH, osmolality, assay, IDD, clarity, visible particles, and subvisible particles. The pH variation (0.1 units over 6 weeks at pH 6.0) was insignificant. There was no evidence that stability is problematic at any of the temperatures tested.

Example 12

A solubility study of dried 2-IB as compared to hydrated 2-IB was performed. Three formulations were prepared, based on formulation #02-5. The 07-1 formulation was obtained from 2-IB "as is" material (i.e., 2-IB taken straight from the vial) after drying. The 07-2 formulation was obtained from 2-IB fully hydrated material by leaving "as is" 2-IB material at 20° C./RH (70±5%). The 07-3 formulation was obtained from 2-IB "as is" material. The solutions were examined for appearance and pH. The water content of the dried material, the "as is" material, and the fully hydrated material was determined as 1%, 12%, and 18% respectively.

Table 12 below presents the amounts of the ingredients used for preparation of the formulations (07-1, 07-2, and 07-3), the time it took to dissolve the 2-IB material (used in each formulation) in the citric acid 0.1 M solution, the final pHs of the three formulations and their appearance.

TABLE 12

|  | 07-1 | 07-2 | 07-3 |
| --- | --- | --- | --- |
| 2-IB conc. | 0.75 mg/g | 0.75 mg/g | 0.75 mg/g |
| 2-IB taken as: | dried | fully hydrated | "as is" |
| Theoretical amount of 2-IB, (g) | 0.157 | 0.157 | 0.157 |
| Water content (%) | 1.3340 | 18.1020 | 11.8330 |
| Water content (%), replicate | 1.2470 | 18.1050 | 11.7900 |
| Water content (%), average | 1.2905 | 18.1035 | 11.8115 |
| Dry 2-IB, % | 98.71 | 81.90 | 88.19 |
| Calculated amount of 2-IB based corrected for water content | 0.1591 | 0.1917 | 0.1780 |
| Actual amount of 2-IB taken, (g) | 0.1605 | 0.1915 | 0.1781 |
| Citric acid 0.1M solution (g) | 20.0 | 20.0 | 20.0 |
| Actual citric acid 0.1M solution (g) | 20.0 | 20.0 | 20.0 |
| Time to dissolve 2-IB (min) | 1.0 | 1.0 | 1.0 |
| Sodium citrate dihydrate 0.1M solution (ca., g) | ~10.0 | ~10.0 | ~10.0 |
| Actual sodium citrate dihydrate 0.1M solution (g) | 23.1 | 23.7 | 23.5 |
| Calculated water for injection to add (up to 200 g) | 160.0 | 160.0 | 160.0 |
| Actual water for injection added (g) | 160.0 | 160.0 | 160.0 |
| Total amount of solution (g) | 203.3 | 203.9 | 203.7 |
| pH (theoretical) | 4.0 | 4.0 | 4.0 |
| pH (actual) | 4.00 | 4.00 | 4.00 |
| Appearance | Clear and colorless | Clear and colorless | Clear and colorless |

Example 13

A terminal sterilization study of two formulations of 2-IB in citrate buffer with or without CAPTISOL® was performed to determine which sterilization methods may be used without degrading 2-IB.

Four (4) buffered 2-IB formulations were prepared including placebo formulations lacking 2-IB. Each of these solutions was filtered through a 0.22 μm PES filter. The pH, osmolality, visual appearance, and 2-IB content were determined. The pH was also determined following titration of the 2-IB citric acid solution with the sodium citrate solution.

Each formulation was divided into 4×10 g portions. Each portion was distributed into a 20 ml glass vial. Each of the four samples was placed in the Tuttnauer steam sterilizer and autoclaved (Program 6 (for liquids, 121° C. for 15 minutes)). Following autoclaving, the samples were allowed to cool down to room temperature. A 5 g sample was taken from each of the four vials for determination of appearance, pH, and osmolality. The remaining 5 g of the formulation were employed for the assay.

Table 24 presents the materials and their amounts used for preparation of each of the four formulations, citrate buffer capacity, visual appearance, pH, and assay before and after terminal sterilization. The assay referred to in Table 24 refers to the stability of the solutions monitored by HPLC analysis. As demonstrated in Table 24, the formulations can be autoclaved without a significant decrease in 2-IB stability.

Example 14

A study was undertaken to assess the potential for in-vivo precipitation of two selected formulations. For this purpose, the In-Vitro Static Serial Model was used as described in Example 6.

Table 25 presents the amounts of the materials used for the 09-1, 09-1V, 09-2, and 09-2V preparations, their buffer capacities, and pH and appearance after titration of the 2-IB citric acid solution with the sodium citrate. Tables 26 and 27 present the appearance and pH values for dilutions of 09-1 and 09-1V in ISPB and dilutions of 09-1 in the vehicle. The appearance and pH results presented in Tables 26 and 27 indicate that for all dilutions performed, both preparations 09-1 and 09-2 do not show precipitation when diluted with Sorensen buffer mimicking physiological pH. Therefore, the risk of in-vivo precipitation of these formulations should be low. In addition, the pH change toward more physiological values is rapid, increasing in-vivo compatibility/safety.

Tables

TABLE 13

Overview of formulation, pH, 2-IB solubility/encapsulated and stability in SBE-CD or HP-CD formulations.

| Formulation | Final pH | 2-IB Solubilized/ encapsulated (mg/ml) | Visual inspection after 12 hours at 5° C. |
|---|---|---|---|
| 2-IB in 40% CAPTISOL ®/WFI | 6.8 | 4.2 | No precipitation |
| 2-IB in 20% CAPTISOL ®/WFI | 6.7 | 2.4 | No precipitation |
| 2-IB in 10% CAPTISOL ®/WFI | 6.5 | 1.5 | No precipitation |
| 2-IB in 5% CAPTISOL ®/WFI | 6.5 | 1.0 | No precipitation |
| 2-IB in 2.5% CAPTISOL ®/WFI | 6.3 | 0.7 | No precipitation |
| 2-IB in 40% CAPTISOL ®/50 mM Citrate pH 5.0 | 5.5 | 9.9 | No precipitation |
| 2-IB in 20% CAPTISOL ®/50 mM Citrate pH 5.0 | 5.3 | 7.0 | No precipitation |
| 2-IB in 10% CAPTISOL ®/50 mM Citrate pH 5.0 | 5.1 | 4.6 | No precipitation |
| 2-IB in 5% CAPTISOL ®/50 mM Citrate pH 5.0 | 5.1 | 2.9 | No precipitation |
| 2-IB in 2.5% CAPTISOL ®/50 mM Citrate pH 5.0 | 5.0 | 1.9 | No precipitation |
| 2-IB in 40% CAPTISOL ®/50 mM Citrate pH 4.0 | 5.1 | 14.5 | No precipitation |
| 2-IB in 20% CAPTISOL ®/50 mM Citrate pH 4.0 | 4.9 | 11.4 | No precipitation |
| 2-IB in 10% CAPTISOL ®/50 mM Citrate pH 4.0 | 4.6 | 8.0 | No precipitation |
| 2-IB In 5% CAPTISOL ®/50 mM Citrate pH 4.0 | 4.4 | 5.5 | No precipitation |
| 2-IB In 2.5% CAPTISOL ®/50 mM Citrate pH 4.0 | 4.3 | 3.7 | Small amount of precipitation |
| 2-IB in 40% KLEPTOSE ® HPB/WFI | 6.7 | 1.2 | No precipitation |
| 2-IB In 20% KLEPTOSE ® HPB/WFI | 6.6 | 0.9 | No precipitation |
| 2-IB in 10% KLEPTOSE ® HPB/WFI | 6.5 | 0.6 | No precipitation |
| 2-IB in 5% KLEPTOSE ® HPB/WFI | 6.5 | 0.5 | No precipitation |
| 2-IB In 2.5% KLEPTOSE ® HPB/WFI | 6.5 | 0.5 | Precipitation |
| 2-IB in 40% KLEPTOSE ® HPB/50 mM Citrate pH 5.0 | 5.6 | 2.6 | No precipitation |
| 2-IB in 20% KLEPTOSE ® HPB/50 mM Citrate pH 5.0 | 5.3 | 2.1 | No precipitation |
| 2-IB in 10% KLEPTOSE ® HPB/50 mM Citrate pH 5.0 | 5.2 | 1.6 | No precipitation |
| 2-IB in 5% KLEPTOSE ® HPB/50 mM Citrate pH 5.0 | 5.1 | 1.2 | No precipitation |
| 2-IB in 2.5% KLEPTOSE ® HPB/50 mM Citrate pH 5.0 | 5.1 | 0.9 | No precipitation |
| 2-IB in 40% KLEPTOSE ® HPB/50 mM Citrate pH 4.0 | 5.0 | 5.6 | No precipitation |
| 2-IB in 20% KLEPTOSE ® HPB/50 mM Citrate pK 4.0 | 4.7 | 5.1 | Precipitation |

TABLE 13-continued

Overview of formulation, pH, 2-IB solubility/encapsulated and stability in SBE-CD or HP-CD formulations.

| Formulation | Final pH | 2-IB Solubilized/encapsulated (mg/ml) | Visual inspection after 12 hours at 5° C. |
|---|---|---|---|
| 2-IB in 10% KLEPTOSE ® HPB/50 mM Citrate pH 4.0 | 4.5 | 4.1 | Precipitation |
| 2-IB in 5% KLEPTOSE ® HPB/50 mM Citrate pH 4.0 | 4.3 | 3.0 | Precipitation |
| 2-IB In 2.5% KLEPTOSE ® HPB/50 mM Citrate pH4.0 | 4.2 | 2.5 | Precipitation |

TABLE 14

Formulations of 2-IB based on SBE-CD at different pH

| Formulations | CAPTISOL ®, % | Citric acid, mM | Sodium citrate, mM | 2-IB, mg/g | Ph |
|---|---|---|---|---|---|
| F429-02-001p002 | 10 | 0.6 | 0.0 | 1.5 | 6.0 |
| F429-02-001p003 | 10 | 2.0 | 0.0 | 2.5 | 5.5 |
| F429-02-001p004 | 10 | 6.6 | 1.5 | 3.9 | 5.0 |
| F429-02-001p007 | 8 | 5.6 | 0.0 | 4.0 | 5.0 |
| F429-02-001p005 | 10 | 15.0 | 0.2 | 7.0 | 4.5 |
| F429-02-001p006 | 10 | 32.3 | 3.5 | 9.7 | 4.0 |

TABLE 15 pH and osmolality of formulations after 6 weeks' storage at three different temperatures

| | | pH | | | | Osmolality, osm/kg | | | |
|---|---|---|---|---|---|---|---|---|---|
| Sample | Storage | T = 0 | T = 2 weeks | T = 4 weeks | T = 6 weeks | T = 0 | T = 2 weeks | T = 4 weeks | T = 6 weeks |
| F429-02-001P002 | 5° C. | 6.0 | 6.0 | 6.0 | 6.0 | 0.287 | 0.292 | 0.239 | 0.288 |
| | 25° C. | | 6.0 | 6.0 | 6.0 | | 0.290 | 0.288 | 0.290 |
| | 40° C. | | 6.0 | 6.0 | 6.0 | | 0.293 | 0.317 | 0.292 |
| F429-02-001P003 | 5° C. | 5.5 | 5.6 | 5.6 | 5.6 | 0.292 | 0.298 | 0.293 | 0.291 |
| | 25° C. | | 5.6 | 5.6 | 5.6 | | 0.296 | 0.293 | 0.292 |
| | 40° C. | | 5.6 | 5.6 | 5.6 | | 0.298 | 0.301 | 0.295 |
| F429-02-001P004 | 5° C. | 5.0 | 5.0 | 5.0 | 5.0 | 0.299 | 0.304 | 0.298 | 0.300 |
| | 25° C. | | 5.0 | 5.0 | 5.0 | | 0.302 | 0.300 | 0.299 |
| | 40° C. | | 5.0 | 5.0 | 5.0 | | 0.303 | 0.306 | 0.300 |
| F429-02-001P005 | 5° C. | 4.5 | 4.5 | 4.5 | 4.6 | 0.311 | 0.316 | 0.312 | 0.311 |
| | 25° C. | | 4.5 | 4.5 | 4.5 | | 0.314 | 0.314 | 0.313 |
| | 40° C. | | 4.5 | 4.5 | 4.5 | | 0.317 | 0.317 | 0.310 |
| F429-02-001P006 | 5° C. | 4.0 | 4.0 | 4.1 | 4.1 | 0.329 | 0.340 | 0.332 | 0.332 |
| | 25° C. | | 4.0 | 4.0 | 4.0 | | 0.332 | 0.330 | 0.327 |
| | 40° C. | | 4.0 | 4.0 | 4.0 | | 0.337 | 0.350 | 0.336 |
| F429-02-001P007 | 5° C. | 5.0 | 5.0 | 5.1 | 5.1 | 0.232 | 0.233 | 0.232 | 0.233 |
| | 25° C. | | 5.0 | 5.0 | 5.1 | | 0.231 | 0.233 | 0.231 |
| | 40° C. | | 5.0 | 5.0 | 5.0 | | 0.235 | 0.236 | 0.234 |

TABLE 16

Purity and content of 2-IB in the six formulations after 6 weeks' storage at three different temperatures

| | F429-02-001p002 | | | F429-02-001p003 | | | F429-02-001p004 | | |
|---|---|---|---|---|---|---|---|---|---|
| Storage | Purity % | Content mg/ml | Recovery % | Purity % | Content mg/ml | Recovery % | Purity % | Content mg/ml | Recovery % |
| T = 0 | 96.9 | 1.59 | 100 | 99.0 | 2.60 | 100 | 99.1 | 4.02 | 100 |
| 2 weeks, 5° C. | 96.6 | 1.64 | 103 | 99.0 | 2.69 | 104 | 99.0 | 4.22 | 105 |
| 2 weeks, 25° C. | 98.8 | 1.62 | 102 | 98.8 | 2.68 | 103 | 99.0 | 4.20 | 104 |
| 2 weeks, 40° C. | 98.7 | 1.61 | 102 | 98.9 | 2.70 | 104 | 99.0 | 4.26 | 106 |
| 4 weeks, 5° C. | 98.5 | 1.64 | 103 | 98.9 | 2.69 | 104 | 98.9 | 4.31 | 107 |
| 4 weeks, 25° C. | 98.5 | 1.63 | 102 | 99.0 | 2.69 | 104 | 98.9 | 4.18 | 104 |

TABLE 16-continued

Purity and content of 2-IB in the six formulations after 6 weeks' storage at three different temperatures

| 4 weeks, 40° C. | 98.5 | 1.60 | 101 | 96.9 | 2.67 | 103 | 98.9 | 4.20 | 104 |
| 6 weeks, 5° C. | 99.3 | 1.69 | 106 | 99.3 | 2.73 | 105 | 99.3 | 4.29 | 107 |
| 6 weeks, 25° C. | 99.3 | 1.64 | 103 | 99.2 | 2.74 | 106 | 99.2 | 4.24 | 105 |
| 6 weeks, 40° C. | 99.3 | 1.64 | 103 | 99.3 | 2.73 | 105 | 99.2 | 4.26 | 106 |

| | F429-02-001p005 | | | F429-02-001p006 | | | F429-02-001p007 | | |
|---|---|---|---|---|---|---|---|---|---|
| Storage | Purity % | Content mg/ml | Recovery % | Purity %. | Content mg/ml | Recovery % | Purity %. | Content mg/ml | Recovery % |
| T = 0 | 99.1 | 7.17 | 100 | 99.1 | 10-01 | 100 | 99.1 | 4.03 | 100 |
| 2 weeks, 5° C. | 99.1 | 7.60 | 106 | 99.1 | 10.49 | 105 | 99.1 | 4.46 | 111 |
| 2 weeks, 25° C. | 99.1 | 7.70 | 107 | 99.1 | 10.43 | 104 | 99.0 | 4.35 | 108 |
| 2 weeks, 40° C. | 99.0 | 7.85 | 110 | 99.1 | 10.72 | 107 | 99.0 | 4.29 | 106 |
| 4 weeks, 5° C. | 99.0 | 7.49 | 105 | 99.0 | 10.42 | 104 | 99.0 | 4.37 | 108 |
| 4 weeks, 25° C. | 99.1 | 7.42 | 104 | 99.0 | 10.42 | 104 | 98.9 | 4.15 | 103 |
| 4 weeks, 40° C. | 98.9 | 7.46 | 104 | 99.0 | 10.42 | 104 | 98.9 | 4.10 | 102 |
| 6 weeks, 5° C. | 99.2 | 7.70 | 107 | 99.2 | 11.23 | 112 | 99.2 | 4.32 | 107 |
| 6 weeks, 25° C. | 99.2 | 7.67 | 107 | 99.2 | 11.01 | 110 | 99.2 | 4.30 | 107 |
| 6 weeks, 40° C. | 99.2 | 7.73 | 108 | 99.1 | 10.86 | 108 | 99.2 | 4.49 | 111 |

TABLE 17

Summary of stability study for 2-IB formulations without cyclodextrin

| | F1 | F2 | F3 | F4 | F5 | F6 | F7 | F8 | F9 |
|---|---|---|---|---|---|---|---|---|---|
| 2-IB (mg/g) | 1 | 1 | 1 | 1 | 1 | 1 | 5 | 4 | 5 |
| NaCl (%) | 0.45 | 0.45 | 0.45 | 0.45 | 0.45 | 0.45 | 0.51 | 0.51 | 0.51 |
| Glucose (%) | 2.5 | 2.5 | 2.5 | 2.5 | 2.5 | 2.5 | 5 | 5 | 5 |
| Citric buffer pH 4.0 (mM) | 0 | 1 | 2.5 | 5 | 7.5 | 10 | 10 | 10 | 5 |
| Appearance after preparation | not clear | not clear | not clear | clear | clear | clear | not clear | not clear | not clear |
| Osmolality (mOsm) | | | | | | 313 | | | |
| pH | | | | 4.43 | 4.31 | 4.23 | | | |
| study: 1st day, 5° C. | | | | ppt | ppt | ppt | | | |
| study: 2nd day, 5° C. | | | | ppt | ppt | ppt | | | |
| study: 3rd day, 5° C. | | | | ppt | ppt | ppt | | | |

| | F10 | F11 | F12 | F13 | F14 | F15 | F16 | F17 | F18 |
|---|---|---|---|---|---|---|---|---|---|
| 2-IB (mg/g) | 3.5 | 3 | 3.5 | 3 | 4 | 5 | 2 | 2.5 | 3 |
| NaCl (%) | 0.73 | 0.73 | 0.73 | 0.51 | 0.51 | 0.51 | 0.73 | 0.73 | 0.73 |
| Glucose (%) | 2.5 | 2.5 | 2.5 | 5 | 5 | 5 | 2.5 | 2.5 | 2.5 |
| Citric buffer pH 4.0 (mM) | 10 | 10 | 5 | 15 | 15 | 15 | 15 | 15 | 15 |
| Appearance after preparation | not clear | not clear | not clear | clear | not clear | not clear | clear | clear | not clear |
| Osmolality (mOsm) | | | | 318 | | | 321 | 321 | |
| pH | | | | 4.66 | | | 4.40 | 4.49 | |
| study: 1st day, 5° C. | | | | clear | | | clear | ppt | |
| study: 2nd day, 5° C. | | | | clear | | | clear | ppt | |
| study: 3rd day, 5° C. | | | | few part. | | | clear | ppt | |

TABLE 18

Summary of stability study for 2-IB formulations with cyclodextrin

| | F19 | F20 | F21 | F22 | F23 | F24 | F25 | F26 | F27 | F28 |
|---|---|---|---|---|---|---|---|---|---|---|
| 2-IB (mg/g) | 2.5 | 2.5 | 2.5 | 2.5 | 2.5 | 3 | 3 | 3 | 3 | 3 |
| NaCl (%) | 0.73 | 0.73 | 0.73 | 0.73 | 0.73 | 0.73 | 0.73 | 0.73 | 0.51 | 0.51 |
| CAPTISOL ® (%) | 2.5 | 2.5 | 2.5 | 2.5 | 2.5 | 2.5 | 2.5 | 2.5 | 5 | 5 |
| Citric buffer pH 4.0 (mM) | 15 | | | | | | | | | |
| Citric acid (mM) | 1.75 | 10 | | 15 | 20 | 10 | 15 | 20 | 10 | 15 |
| Citric buffer pH 3.5 (mM) | | | 15 | | | | | | | |
| Sodium citrate (100 mM) | | 4 | 1.5 | 9.5 | 4 | 1.6 | 7.45 | 11.2 | 1 | 5.75 |
| Appearance after preparation | clear | clear | clear | clear | clear | clear | clear | clear | clear | clear |
| Total molarity (mM) | 16.8 | 14 | 16.5 | 24.5 | 24 | 11.6 | 22.5 | 31.2 | 11 | 20.8 |
| Osmolality (mOsm) | 321 | 319 | 320 | 340 | 360 | 306 | 333 | 356 | 308 | 323 |
| pH | 4.01 | 3.99 | 4.00 | 4.00 | 4.00 | 4.00 | 4.00 | 4.00 | 4.01 | 4.00 |
| study: 1st day, 5° C. | clear | clear | clear | clear | clear | clear | ppt | clear | clear | clear |
| study: 2nd day, 5° C. | ppt | clear | clear | clear | clear | clear | ppt | clear | clear | clear |
| study: 3rd day, 5° C. | ppt | clear | clear | clear | clear | few part. | ppt | clear | clear | clear |

| | F29 | F30 | F31 | F32 | F33 | F34 | F35 | F36 | F37 | F38 |
|---|---|---|---|---|---|---|---|---|---|---|
| 2-IB (mg/g) | 3 | 4 | 4 | 4 | 5 | 5 | 5 | 3 | 4 | 5 |
| NaCl (%) | 0.51 | 0.51 | 0.51 | 0.51 | 0.51 | 0.51 | 0.51 | 0.73 | 0.51 | 0.51 |
| CAPTISOL ® (%) | 5 | 5 | 5 | 5 | 5 | 5 | 5 | 2.5 | 5 | 5 |
| Citric buffer pH 4.0 (mM) | | | | | | | | | | |
| Citric acid (mM) | 20 | 10.8 | 15 | 20 | 14.2 | 15.3 | 20 | | 2.75 | 5 |
| Citric buffer pH 3.5 (mM) | | | | | | | | 20 | 20 | 20 |
| Sodium citrate (100 mM) | 10.3 | 0.25 | 1 | 4.8 | | | | 5.15 | 0.25 | |
| Appearance after preparation | clear | clear | clear | clear | clear | clear | clear | clear | clear | clear |
| Total molarity (mM) | 30.3 | 11 | 16 | 24.8 | 14.2 | 15.3 | 25.2 | 20.2 | 22.8 | 25 |
| Osmolality (mOsm) | 345 | 307 | 307 | 326 | 307 | 309 | 333 | 328 | 326 | 330 |
| pH | 4.00 | 4.00 | 3.98 | 3.97 | 4.01 | 3.99 | 3.99 | 4.00 | 3.99 | 3.99 |
| study: 1st day, 5° C. | clear | clear | clear | clear | ppt | clear | clear | clear | clear | ppt |
| study: 2nd day, 5° C. | clear | clear | clear | clear | ppt | clear | clear | few part. | clear | ppt |
| study: 3rd day, 5° C. | clear | clear | clear | clear | ppt | few part. | ppt | ppt | clear | ppt | ppt: precipitation;
few part: a few particles are visible

TABLE 19

Three-day stability study results for formulation F30 (Table 19A) and formulation F34 (Table 19B).

| | T-0 | T-1st day | | | T-2nd day | | | T-3rd day | | |
|---|---|---|---|---|---|---|---|---|---|---|
| | | 5° C. | 25° C. | 40° C. | 5° C. | 25° C. | 40° C. | 5° C. | 25° C. | 40° C. |
| Table 19A | | | | | | | | | | |
| 2-IB assay (mg/g) | 4.0 | 4.0 | 4.0 | 4.0 | 4.1 | 4.0 | 4.1 | 4.0 | 4.0 | 4.1 |
| pH | 4.2 | 4.2 | 4.2 | 4.2 | 4.2 | 4.2 | 4.2 | 4.2 | 4.2 | 4.2 |
| Appearance | Clear solution | Clear solution | Clear solution | Clear solution | Clear solution | Clear solution | Clear solution | Clear solution | Clear solution | Clear solution |
| Table 19B | | | | | | | | | | |
| 2-IB assay (mg/g) | 5.0 | 5.0 | 5.0 | 5.0 | 5.0 | 5.1 | 5.1 | 5.1 | 5.1 | 5.1 |
| pH | 4.2 | 4.2 | 4.2 | 4.2 | 4.2 | 4.1 | 4.2 | 4.1 | 4.2 | 4.2 |
| Appearance | Clear solution | Clear solution | Clear solution | Clear solution | Clear solution | Clear solution | Clear solution | Clear solution | Clear solution | Clear solution |

TABLE 20

Composition of 2-IB formulations (0, 0.6, 0.75, and 1.0 mg/g) in citrate buffer (pH = 4.0 ± 0.2), and appearance and pH values for each formulation at time points T = 0, 1, 2, and 3 days stored in temperature chambers at 5° C. ± 3° C. and 25° C. ± 2° C.

|  | 01-1 | 01-2 | 01-3 | 01-4 | 01-5 | 01-6 | 01-7 | 01-8 | 01-9 | 01-10 | 01-11 | 01-12 |
|---|---|---|---|---|---|---|---|---|---|---|---|---|
| 2-IB conc. (mg/g) | 0 | 0 | 0 | 0.6 | 0.6 | 0.6 | 0.75 | 0.75 | 0.75 | 1.0 | 1.0 | 1.0 |
| 2-IB (95.8%), g | 0 | 0 | 0 | 0.01 | 0.01 | 0.01 | 0.01 | 0.01 | 0.01 | 0.02 | 0.02 | 0.02 |
| Citric acid 0.1M solution (g) | 2.0 | 2.0 | 2.0 | 2.0 | 2.0 | 2.0 | 2.0 | 2.0 | 2.0 | 2.0 | 2.0 | 2.0 |
| Sodium citrate dihydrate 0.1M solutiamouon (g) | 1.21 | 1.50 | 1.82 | 0.94 | 1.45 | 1.69 | 1.03 | 1.27 | 1.58 | 1.01 | 1.30 | 1.49 |
| Water for Injection | Up to 20 g | Up to 20 g | Up to 20 g | Up to 20 g | Up to 20 g | Up to 20 g | Up to 20 g | Up to 20 g | Up to 20 g | Up to 20 g | Up to 20 g | Up to 20 g |
| Total molarity, mM | 16.0 | 17.4 | 19.0 | 14.6 | 17.2 | 18.4 | 15.1 | 16.3 | 17.9 | 15.0 | 16.4 | 17.4 |
| pH Target | 3.8 | 4.0 | 4.2 | 3.8 | 4.0 | 4.2 | 3.8 | 4.0 | 4.2 | 3.8 | 4.0 | 4.2 |
| pH obtained after titration (T-0) | 3.81 | 4.00 | 4.20 | 3.78 | 3.99 | 4.19 | 3.81 | 3.99 | 4.19 | 3.80 | 4.00 | 4.20 |
| STS: 1st day, pH 5° C. | 3.99 | 4.19 | 4.43 | 4.08 | 4.28 | 4.41 | 4.07 | 4.12 | —[1] | 3.72 | —[2] | —[2] |
| STS: 3rd day, pH | 3.83 | 4.02 | 4.22 | 3.79 | 4.08 | 4.22 | 3.80 | 4.03 | —[2] | 3.82 | —[2] | —[2] |
| STS: 1st day, pH 25° C. | 4.00 | 4.00 | 4.27 | 3.91 | 4.23 | 4.21 | 3.98 | 4.14 | 4.29 | 4.02 | 4.25 | 4.21 |
| STS: 3rd day, pH | 3.81 | 4.02 | 4.22 | 3.91 | 4.08 | 4.28 | 3.80 | 4.11 | 4.13 | 3.92 | 4.08 | 4.15 |
| STS: 1st day, appearance 5° C. | clear | clear | clear | clear | clear | clear | clear | clear | ppt[2] | clear | ppt[3] | ppt[3] |
| STS: 2nd day, appearance | clear | clear | clear | clear | clear | clear | clear | clear | ppt[3] | clear | ppt[3] | ppt[3] |
| STS: 3rd day, appearance | clear | clear | clear | clear | clear | clear | clear | clear | ppt[3] | clear | ppt[3] | ppt[3] |
| STS: 1st day, appearance 25° C. | clear | clear | clear | clear | clear | clear | clear | clear | clear | clear | clear | clear |
| STS: 2nd day, appearance | clear | clear | clear | clear | clear | clear | clear | clear | clear | clear | clear | clear |
| STS: 3rd day, appearance | clear | clear | clear | clear | clear | clear | clear | clear | clear | clear | clear | clear |

[1] pH in vials with precipitation was not measured
[2] ppt—needle-type precipitate

TABLE 21

Amounts of ingredients used to prepare 2-IB formulations (0 (placebo), 0.75, and 1.0 mg/g) in citrate buffer (pH = 4.0 ± 0.2), and appearance and ph values for each formulation at timepoints T = 0, 1, 2, and 3 days stored in temperature chambers at 15° C. ± 3° C. and 25° C. ± 2° C.

|  | 02-1 | 02-2 | 02-3 | 02-4 | 02-5 | 02-6 | 02-7 | 02-8 | 02-9 |
|---|---|---|---|---|---|---|---|---|---|
| 2-IB conc. (mg/g) | 0 | 0 | 0 | 0.75 | 0.75 | 0.75 | 1.0 | 1.0 | 1.0 |
| 2-IB (95.8%), g | 0 | 0 | 0 | 0.0157 | 0.0157 | 0.0157 | 0.0209 | 0.0209 | 0.0209 |
| Citric acid 0.1M solution (g) | 2.0 | 2.0 | 2.0 | 2.0 | 2.0 | 2.0 | 2.0 | 2.0 | 2.0 |
| Sodium Citrate dihydrate 0.1M solution (g) | 1.07 | 1.26 | 1.56 | 0.82 | 1.03 | 1.34 | 0.73 | 0.96 | 1.33 |
| Water for Injection | Up to 20 g | Up to 20 g | Up to 20 g | Up to 20 g | Up to 20 g | Up to 20 g | Up to 20 g | Up to 20 g | Up to 20 g |
| Total molarity, mM | 15.35 | 16.30 | 17.80 | 14.10 | 15.15 | 16.70 | 13.65 | 14.80 | 16.65 |
| pH Target | 3.8 | 4.0 | 4.2 | 3.8 | 4.0 | 4.2 | 3.8 | 4.0 | 4.2 |
| pH obtained after titration (T-0) | 3.79 | 3.97 | 4.21 | 3.82 | 4.03 | 4.23 | 3.80 | 4.03 | 4.24 |
| STS: 1st day, pH 15° C. | 3.81 | 4.04 | 4.23 | 3.81 | 4.07 | 4.22 | 3.82 | 4.05 | 4.29 |
| STS: 2nd day, pH | 3.84 | 4.02 | 4.25 | 3.87 | 4.05 | 4.27 | 3.82 | 4.04 | 4.27 |
| STS: 3rd day, pH | 3.81 | 4.02 | 4.27 | 3.83 | 4.04 | 4.24 | 3.83 | 4.05 | 4.28 |
| STS: 1st day, pH 25° C. | 3.80 | 3.97 | 4.19 | 3.82 | 4.03 | 4.20 | 3.81 | 4.05 | 4.29 |
| STS: 2nd day, pH | 3.83 | 4.05 | 4.25 | 3.84 | 4.04 | 4.27 | 3.85 | 4.02 | 4.25 |
| STS: 3rd day, pH | 3.80 | 4.00 | 4.22 | 3.81 | 4.04 | 4.27 | 3.82 | 4.06 | 4.33 |
| STS: 1st day, appearance 15° C. | clear | clear | clear | clear | clear | clear | clear | clear | ppt |
| STS: 2nd day, appearance | clear | clear | clear | clear | clear | clear | clear | clear | ppt |
| STS: 3rd day, appearance | clear | clear | clear | clear | clear | clear | clear | clear | ppt |
| STS: 1st day, appearance 25° C. | clear | clear | clear | clear | clear | clear | clear | clear | clear |
| STS: 2nd day, appearance | clear | clear | clear | clear | clear | clear | clear | clear | clear |
| STS: 3rd day, appearance | clear | clear | clear | clear | clear | clear | clear | clear | clear |

TABLE 22

Composition of 2-IB isotonic formulations (0.75, 1.0, 2.0, and 4.0 mg/g) in citrate buffer (pH = 4.0-6.2), and appearance and pH values for each formulation at time points T = 0, 1, 2, and 3 days stored at 5° C. ± 3° C. and 25° C. ± 2° C.

| | 03-1 | 03-2 | 03-3 | 03-4 | 03-5 | 03-6 | 03-7 | 03-8 | 03-9 | 10-03 | 03-11 | 03-12 | 13-03 | 03-14 | 15-03 | 16-03 |
|---|---|---|---|---|---|---|---|---|---|---|---|---|---|---|---|---|
| 2-IB conc., mg/g | 4.0 | 4.0 | 4.0 | 2.0 | 2.0 | 2.0 | 2.0 | 2.0 | 1.0 | 1.0 | 1.0 | 1.0 | 1.0 | 0.75 | 0.75 | 0.75 |
| 2-IB (95.8%), g | 0.084 | 0.084 | 0.084 | 0.042 | 0.042 | 0.042 | 0.042 | 0.042 | 0.021 | 0.021 | 0.021 | 0.021 | 0.021 | 0.016 | 0.016 | 0.016 |
| Citric acid 0.1M solution (g) | 2.3126 | 1.9184 | 1.4089 | 1.906 | 1.3898 | 0.9029 | 0.5036 | 0.2966 | 1.915 | 1.4181 | 0.9071 | 0.5216 | 0.3167 | 0.8936 | 0.5131 | 0.3133 |
| 25% CAPTISOL®/ 2.45% NaCl stock solution, (g) | 4.1625 | 3.9998 | 3.9897 | 4.0215 | 3.9907 | 3.9945 | 4.0165 | 3.9808 | 4.0079 | 4.0274 | 4.1164 | 4.0249 | 4.0381 | 3.9893 | 4.0238 | 4.0385 |
| Sodium Citrate dihydrate 0.1M solution (g) | 0 | 0.4639 | ppt | 1.375 | 2.1573 | 2.4214 | 3.6295 | ppt | 2.0182 | 2.4845 | 3.0597 | 4.14459 | 3.6235 | 3.242 | 4.474 | 3.9582 |
| Water for Injection (g) | 2.5201 | 1.7929 | Ppt | 1.7143 | 1.5042 | 1.7132 | 0.8506 | ppt | 1.1265 | 1.1116 | 0.9796 | 0.3312 | 1.0627 | 0.8159 | 0 | 0.8276 |
| Total molarity, mM | 11.26 | 11.91 | 7.04 | 16.41 | 17.74 | 16.62 | 20.67 | 1.48 | 19.67 | 19.51 | 19.83 | 23.34 | 19.70 | 20.68 | 24.94 | 21.36 |
| pH Target | 4.0 | 4.5 | 5.0 | 4.5 | 5.0 | 5.5 | 6.0 | 6.2 | 4.5 | 5.0 | 5.5 | 6.0 | 6.2 | 5.5 | 6.0 | 6.2 |
| pH obtained after titration (T-0) | 3.93 | 4.50 | ppt | 4.49 | 5.09 | 5.52 | ppt | ppt | 4.53 | 5.01 | 5.52 | 6.01 | 6.23 | 5.52 | 6.02 | 6.23 |
| STS: 1st day, 5° C. pH | 4.04 | ppt | ppt | 4.52 | 5.14 | ppt | ppt | ppt | 4.59 | 5.05 | 5.53 | 6.02 | ppt | 5.55 | 6.02 | 6.21 |
| STS: 2nd day, pH | 4.03 | ppt | ppt | 4.54 | 5.11 | ppt | ppt | ppt | 4.55 | 5.00 | 5.50 | 5.96 | ppt | 5.49 | 5.98 | 6.19 |
| STS: 3rd day, pH | 4.10 | ppt | ppt | 4.57 | ppt | 5.51 | ppt | ppt | 4.58 | 5.04 | 5.50 | 5.95 | 6.20 | 5.52 | 5.99 | 6.17 |
| STS: 1st day, 25° C. pH | 4.02 | 4.53 | ppt | 4.52 | 5.10 | ppt | ppt | ppt | 4.54 | 5.03 | 5.48 | 5.97 | 6.20 | 5.51 | 5.97 | 6.17 |
| STS: 2nd day, pH | 4.06 | 4.58 | ppt | 4.58 | 5.15 | ppt | ppt | ppt | 4.53 | 5.03 | 5.52 | 5.98 | 6.14 | 5.52 | 5.99 | 6.18 |
| STS: 3rd day, pH | 4.08 | 4.58 | ppt | 4.57 | 5.13 | ppt | ppt | ppt | 4.57 | 5.02 | 5.49 | 5.95 | | 5.51 | 5.93 | 6.18 |
| Osmolality obtained after titration (T-0) RT | 293 | 299 | ppt | 300 | 304 | 309 | ppt | ppt | 309 | 312 | 326 | 333 | 325 | 320 | 337 | 329 |
| STS: 3rd day, osmolality, mOsm 5° C. | 293 | ppt | ppt | 300 | ppt | ppt | ppt | ppt | 308 | 312 | 328 | 332 | ppt | 321 | 337 | 330 |
| STS: 3rd day, osmolality, mOsm 25° C. | 290 | 297 | ppt | 300 | 302 | ppt | ppt | ppt | 308 | 313 | 327 | 335 | 328 | 317 | 336 | 329 |

TABLE 22-continued

Composition of 2-IB isotonic formulations (0.75, 1.0, 2.0, and 4.0 mg/g) in citrate buffer (pH = 4.0-6.2), and appearance and pH values for each formulation at time points T = 0, 1, 2, and 3 days stored at 5° C. ± 3° C. and 25° C. ± 2° C.

| | | 03-1 | 03-2 | 03-3 | 03-4 | 03-5 | 03-6 | 03-7 | 03-8 | 03-9 | 10-03 | 03-11 | 03-12 | 13-03 | 03-14 | 15-03 | 16-03 |
|---|---|---|---|---|---|---|---|---|---|---|---|---|---|---|---|---|---|
| Appearance obtained after titration (T-0) | RT | clear | clear | ppt | clear | clear | clear | ppt | ppt | clear | clear | clear | clear | clear | clear | clear | clear |
| STS: 1st day, appearance | 5° C. | clear | ppt | ppt | clear | clear | ppt | ppt | ppt | clear | clear | clear | clear | clear | clear | clear | clear |
| STS: 2nd day, appearance | | clear | ppt | ppt | clear | clear | ppt | ppt | ppt | clear | clear | clear | clear | ppt | clear | clear | clear |
| STS: 3rd day, appearance | | clear | ppt | ppt | clear | ppt | clear | ppt | ppt | clear | clear | clear | clear | ppt | clear | clear | clear |
| STS: 1st day, appearance | 25° C. | clear | clear | ppt | clear | clear | ppt | ppt | ppt | clear | clear | clear | clear | clear | clear | clear | clear |
| STS: 2nd day, appearance | | clear | clear | ppt | clear | clear | ppt | ppt | ppt | clear | clear | clear | clear | clear | clear | clear | clear |
| STS: 3rd day, appearance | | clear | clear | ppt | clear | clear | ppt | ppt | ppt | clear | clear | clear | clear | clear | clear | clear | clear |

TABLE 23

Composition of 2-IB placebo isotonic formulations in citrate buffer
(pH = 4.0-6.2) with CAPTISOL ®, and appearance and pH values for each formulation
at time points T = 0, 1, 2, and 3 days stored at 5° C. ± 3° C. and 25° C. ± 2° C.

|  |  | 03-1 | 03-2 | 03-3 | 03-4 | 03-5 | 03-6 |
|---|---|---|---|---|---|---|---|
| 2-IB conc., mg/g |  | 0 | 0 | 0 | 0 | 0 | 0 |
| 2-IB (95.8%), g |  | 0 | 0 | 0 | 0 | 0 | 0 |
| Citric acid 0.1M solution (g) |  | 2.3681 | 1.8622 | 1.4556 | 0.8859 | 0.5515 | 0.3351 |
| 25% CAPTISOL ®/2.45% NaCl stock solution, (g) |  | 4.1152 | 3.9825 | 3.9939 | 3.9852 | 3.8414 | 3.9901 |
| Sodium Citrate dihydrate 0.1M solution (g) |  | 1.8553 | 2.4737 | 3.5027 | 3.9749 | 5.6267 | 5.0957 |
| Water for Injection |  | 1.6782 | 1.7153 | 1.1384 | 1.2175 | 0.0597 | 0.5445 |
| Total molarity, mM |  | 21.12 | 21.6795 | 24.7915 | 24.304 | 30.891 | 27.154 |
| pH Target |  | 4.0 | 4.5 | 5.0 | 5.5 | 6.0 | 6.2 |
| pH obtained after titration (T-0) |  | 4.04 | 4.51 | 5.03 | 5.48 | 5.95 | 6.16 |
| STS: 1$^{st}$ day, pH | 5° C. | 4.02 | 4.52 | 5.04 | 5.50 | 5.97 | 6.18 |
| STS: 2$^{nd}$ day, pH |  | 4.11 | 4.59 | 5.09 | 5.52 | 5.97 | 6.17 |
| STS: 3$^{rd}$ day, pH |  | 4.10 | 4.56 | 5.08 | 5.51 | 5.97 | 6.18 |
| STS: 1$^{st}$ day, pH | 25° C. | 4.06 | 4.54 | 5.06 | 5.53 | 6.02 | 6.21 |
| STS: 2$^{nd}$ day, pH |  | 4.11 | 4.58 | 5.09 | 5.52 | 5.99 | 6.16 |
| STS: 3$^{rd}$ day, pH |  | 4.12 | 4.58 | 5.08 | 5.52 | 5.98 | 6.19 |
| Osmolality obtained after titration (T-0) | RT | 316 | 312 | 326 | 331 | 342 | 347 |
| STS: 3$^{rd}$ day, osmolality, mOsm | 5° C. | 314 | 312 | 326 | 331 | 341 | 342 |
| STS: 3$^{rd}$ day, osmolality, mOsm | 25° C. | 314 | 313 | 328 | 331 | 344 | 345 |
| Appearance obtained after titration (T-0) | RT | clear | clear | clear | clear | clear | clear |
| STS: 1$^{st}$ day, appearance | 5° C. | clear | clear | clear | clear | clear | clear |
| STS: 2$^{nd}$ day, appearance |  | clear | clear | clear | clear | clear | clear |
| STS: 3$^{rd}$ day, appearance |  | clear | clear | clear | clear | clear | clear |
| STS: 1$^{st}$ day, appearance | 25° C. | clear | clear | clear | clear | clear | clear |
| STS: 2$^{nd}$ day, appearance |  | clear | clear | clear | clear | clear | clear |
| STS: 3$^{rd}$ day, appearance |  | clear | clear | clear | clear | clear | clear |

TABLE 24

Materials and their amounts used for preparation of each of the four formulations 08-1, 08-2, 08-1P, and 08-2P, citrate
buffer capacity, visual appearance, pH, and assay before and after terminal sterilization. Water for irrigation is a sterile,
hypotonic, nonpyrogenic irrigating fluid entirely composed of Sterile Water for Injection USP.

|  | 08-1 | 08-1P | 08-2 | 08-2P |
|---|---|---|---|---|
|  | 2-IB conc. | | | |
|  | 0.75 mg/ml | 0.75 mg/ml | 0.75 mg/ml | 0.75 mg/ml |
| Theoretical amount of 2-IB (g) | 0.0345 |  | 0.0345 |  |
| Water content, % | 14.57 |  | 14.57 |  |
| Amount of 2-IB (actual, g) | 0.0402 |  | 0.0404 |  |
| Citric acid 0.1M solution (theoretical, g) | 4.4 | 4.05 | 0.679 | 0.590 |
| Actual citric acid 0.1M solution (g) | 4.4117 | 4.0468 | 0.6927 | 0.5916 |
| Sodium citrate dihydrate 0.1M solution (theoretical, g) | 2.2~ | 2.2~ | ~5.3 | ~5.0 |
| Actual sodium citrate dihydrate 0.1M solution (g) | 2.8465 | 3.1900 | 6.6017 | 6.9156 |
| 4.5% NaCl stock solution, (theoretical, g) | 8.8 | 8.8 |  |  |
| 4.5% NaCl stock solution, (actual, g) | 8.7941 | 8.8272 |  |  |
| 25% CAPTISOL ®/2.45% NaCl stock solution (theoretical, g) |  |  | 8.8 | 8.8 |
| 25% CAPTISOL ®/2.45% NaCl stock solution (actual, g) |  |  | 8.8090 | 8.8511 |
| Water for irrigation (g) | Up to 44 g | Up to 44 g | Up to 44 g | Up to 44 g |
| Actual water for irrigation added (g) | 17.6077 | 18.7046 | 18.7120 | 17.6075 |
| Total formulation (g) | 43.9392 | 44.0253 | 44.0012 | 43.9909 |
| Theoretical buffer capacity, mM | 15.15 | 15.15 | 15.00 | 15.00 |
| Actual buffer capacity, mM | 16.50 | 16.45 | 16.58 | 17.06 |
| pH Target | 4.0 | 4.0 | 6.0 | 6.0 |
| pH obtained after titration (T-0) | 4.0 | 4.0 | 6.0 | 6.0 |

TABLE 24-continued

Materials and their amounts used for preparation of each of the four formulations 08-1, 08-2, 08-1P, and 08-2P, citrate buffer capacity, visual appearance, pH, and assay before and after terminal sterilization. Water for irrigation is a sterile, hypotonic, nonpyrogenic irrigating fluid entirely composed of Sterile Water for Injection USP.

|  | 08-1 | 08-1P | 08-2 | 08-2P |
|---|---|---|---|---|
|  | 2-IB conc. | | | |
|  | 0.75 mg/ml | 0.75 mg/ml | 0.75 mg/ml | 0.75 mg/ml |
| Appearance before sterilization | Clear and colorless | | | |
| Appearance after sterilization | Clear and colorless | | | |
| pH before sterilization | 4.01 | 4.01 | 6.04 | 6.05 |
| pH following sterilization | 4.05 | 4.06 | 6.09 | 6.12 |
| Osmolality before sterilization | 310 | 313 | 309 | 308 |
| Osmolality after sterilization | 314 | 311 | 306 | 306 |
| Assay before sterilization | 99.6% | ND | 99.1% | ND |
| Assay after sterilization | 96.6% | ND | 98.8% | ND |

TABLE 25

Ingredient amounts used for preparing 09-1 formulations and 09-1V (vehicle (placebo) of 09-1), 09-2 and 09-2v (vehicle (placebo) of 09-2) solutions (including buffer capacities, and pH and appearance after titration of the 2-IB citric acid solution with sodium citrate.

|  | Formulation No. | | | |
|---|---|---|---|---|
|  | 09-1 | 09-1V (Placebo) | 09-2 | 09-2V (Placebo) |
|  | 2-1B conc. | | | |
|  | 0.75 mg/g | 0.00 | 0.75 mg/g | 0.00 |
| Theoretical amount of 2-IB (g) | 0.0345 | 0.00 | 0.0345 | 0.00 |
| Weighed amount of 2-IB (g) | 0.0347 | — | 0.0346 | — |
| Water content, % | 6.072 | — | 6.072 | — |
| Water content, g | 0.0021 | — | 0.0021 | — |
| Amount of 2-IB (actual, g) | 0.0326 | — | 0.0325 | — |
| Citric acid 0.1M solution (theoretical, g) | 4.4 | 20.44 | 0.679 | 2.946 |
| Actual citric acid 0.1M solution (g) | 4.4408 | 20.47 | 0.6843 | 2.947 |
| 4.50% NaCl stock solution, (theoretical, g) | 8.8 | 44.00 | — | — |
| 4.50% NaCl stock solution, (actual, g) | 8.8102 | 44.00 | — | — |
| 25% CAPTISOL ®/2.45% NaCl stock solution (theoretical, g) | — | — | 8.8 | 44.00 |
| 25% CAPTISOL ®/2.45% NaCl stock solution (actual, g) | — | — | 8.8629 | 44.022 |
| Sodium citrate dihydrate 0.1M solution (theoretical, g) | 1.80~ | 11.00~ | ~4.0 | ~17.00 |
| Actual sodium citrate dihydrate 0.1M solution (g) | 3.5734 | 17.8140 | 9.5472 | 31.8830 |
| Water for injection (g) | Up to 44.00 | Up to 220.00 | Up to 44.00 | Up to 220.00 |
| Water for injection (actual, g) | 43.9591 | 220.02 | 44.029 | 220.042 |
| Theoretical buffer capacity, mM | 15.15 | 15.15 | 15.00 | 15.00 |
| Actual buffer capacity molarity, mM | 18.23 | 17.40 | 23.24 | 15.83 |
| pH Target | 4.0 | 4.0 | 6.0 | 6.0 |
| pH obtained after titration | 4.17 | 4.06 | 6.17 | 6.09 |
| Appearance after titration | Clear without precipitation | Clear without precipitation | Clear without precipitation | Clear without precipitation |

TABLE 26

Appearance and pHs of 09-1 formulations and 09-1V dilutions with ISPB and with the vehicle.

| Diluting Agent | Formulations to be diluted | Dilution no. | Fold-Dilution | Appearance right after mixing | Appearance after water bath | Appearance following centrifuging | pH |
|---|---|---|---|---|---|---|---|
| ISPB | 09-1 | 1 | 0.5 | Clear Without Precipitation Colorless | Clear Without Precipitation Colorless | Clear Without Precipitation Colorless | 6.78 6.81 |
|  |  | 2 | 0.25 |  |  |  | 7.20 7.19 |

TABLE 26-continued

Appearance and pHs of 09-1 formulations and 09-1V dilutions with ISPB and with the vehicle.

| Diluting Agent | Formulations to be diluted | Dilution no. | Fold-Dilution | Appearance right after mixing | Appearance after water bath | Appearance following centrifuging | pH |
|---|---|---|---|---|---|---|---|
| | | 3 | 0.125 | | | | 7.33 |
| | | | | | | | 7.30 |
| | | 4 | 0.0625 | | | | 7.34 |
| | | | | | | | 7.42 |
| | | 5 | 0.03125 | | | | 7.40 |
| | | | | | | | 7.43 |
| | | 6 | 0.01563 | | | | 7.44 |
| | | | | | | | 7.45 |
| | | 7 | 0.007875 | | | | 7.47 |
| | | | | | | | 7.45 |
| | 09-1V | 1 | 0.5 | Clear Without Precipitation Colorless | Clear Without Precipitation Colorless | Clear Without Precipitation Colorless | 6.85 6.84 |
| | | 2 | 0.25 | | | | 7.17 7.14 |
| | | 3 | 0.125 | | | | 7.36 |
| | | | | | | | 7.33 |
| | | 4 | 0.0625 | | | | 7.39 |
| | | | | | | | 7.41 |
| | | 5 | 0.03125 | | | | 7.42 |
| | | | | | | | 7.45 |
| | | 6 | 0.01563 | | | | 7.46 ND |
| | | 7 | 0.007875 | | | | 7.43 ND |
| Vehicle | 09-1 | 1 | 0.5 | Clear Without Precipitation Colorless | Clear Without Precipitation Colorless | Clear Without Precipitation Colorless | 4.17 4.13 |
| | | 2 | 0.25 | | | | 4.13 4.11 |
| | | 3 | 0.125 | | | | 4.09 4.11 |
| | | 4 | 0.0625 | | | | 4.11 4.11 |
| | | 5 | 0.03125 | | | | 4.09 4.07 |
| | | 6 | 0.01563 | | | | 4.13 4.13 |
| | | 7 | 0.007875 | | | | 4.12 4.09 |

TABLE 27

Appearance and pHs of 09-2 and 09-1V dilutions with ISPB and of 09-2 with the vehicle.

| Diluting Agent | Formulations to be diluted | Dilution no. | Fold-Dilution | Appearance right after mixing | Appearance after water bath | Appearance following centrifuging | pH |
|---|---|---|---|---|---|---|---|
| ISPB | 09-2 | 1 | 0.5 | Clear Without Precipitation Colorless | Clear Without Precipitation Colorless | Clear Without Precipitation Colorless | 7.33 7.33 |
| | | 2 | 0.25 | | | | 7.32 7.39 |
| | | 3 | 0.125 | | | | 7.46 7.39 |
| | | 4 | 0.0625 | | | | 7.46 7.43 |
| | | 5 | 0.03125 | | | | 7.47 7.46 |
| | | 6 | 0.01563 | | | | 7.42 7.43 |
| | | 7 | 0.007875 | | | | 7.45 ND |
| | 09-2V | 1 | 0.5 | Clear Without Precipitation Colorless | Clear Without Precipitation Colorless | Clear Without Precipitation Colorless | 7.31 7.34 |
| | | 2 | 0.25 | | | | 7.43 7.41 |
| | | 3 | 0.125 | | | | 7.41 7.40 |
| | | 4 | 0.0625 | | | | 7.44 7.43 |

TABLE 27-continued

Appearance and pHs of 09-2 and 09-1V dilutions with ISPB and of 09-2 with the vehicle.

| Diluting Agent | Formulations to be diluted | Dilution no. | Fold-Dilution | Appearance right after mixing | Appearance after water bath | Appearance following centrifuging | pH |
|---|---|---|---|---|---|---|---|
| | | 5 | 0.03125 | | | | 7.47 |
| | | | | | | | 7.43 |
| | | 6 | 0.01563 | | | | 7.45 |
| | | | | | | | 7.39 |
| | | 7 | 0.007875 | | | | 7.43 |
| | | | | | | | 7.40 |
| Vehicle | 09-2 | 1 | 0.5 | Clear Without Precipitation Colorless | Clear Without Precipitation Colorless | Clear Without Precipitation Colorless | 6.23 |
| | | | | | | | 6.25 |
| | | 2 | 0.25 | | | | 6.21 |
| | | | | | | | 6.16 |
| | | 3 | 0.125 | | | | 6.10 |
| | | | | | | | 6.14 |
| | | 4 | 0.0625 | | | | 6.18 |
| | | | | | | | 6.16 |
| | | 5 | 0.03125 | | | | 6.16 |
| | | | | | | | 6.17 |
| | | 6 | 0.01563 | | | | 6.16 |
| | | | | | | | 6.17 |
| | | 7 | 0.007875 | | | | 6.09 |
| | | | | | | | 6.10 |

What is claimed is:

1. An aqueous, soluble formulation of 2-iminobiotin, having a pH between 3 and 7, and comprising:
   0.5 mg/ml or more of 2-iminobiotin, and
   between 2.5 to 40% of a substituted beta-cyclodextrin,
   wherein the substituted beta-cyclodextrin is selected from sulfobutyl-ether-beta cyclodextrin (SBE-CD) and hydroxyipropyl-beta cyclodextrin.

2. The formulation according to claim 1 having a pH between 4 and 7, and comprising 2 mg/ml or more of 2-iminobiotin and 2.5 to 20% of a substituted beta-cyclodextrin.

3. The formulation according to claim 1 having a pH between 4 and 6.5, and comprising 0.5 to 3.5 mg/ml or more of 2-iminobiotin and between 5 to 40% of a substituted beta-cyclodextrin.

4. The formulation according to claim 2 having a pH of 4 and comprising 3.5 mg/ml or more of 2-iminobiotin and between 2.5 to 40% of a substituted beta-cyclodextrin.

5. The formulation according to claim 1 having a pH between 4 and 5 and comprising between 0.5 to 5 mg/ml of 2-iminobiotin, and 2.5 to 5% of SBE-CD.

6. The formulation of claim 3, comprising between 5% and 10% SBE-CD.

7. The formulation of claim 4, comprising between 2.5% and 10% SBE-CD.

8. The formulation of claim 5, comprising between 4 mg/ml and 5 mg/ml of 2-iminobiotin.

9. A method of treating perinatal asphyxia in a neonate, the method comprising:
   administering the formulation according to claim 1 to a neonate in need thereof or to the neonate's mother, to treat perinatal asphyxia in the neonate.

10. The method of claim 9, wherein the formulation is administered to the neonate's mother prior to and/or during labor.

11. The method according to claim 9, wherein the treatment further comprises subjecting the neonate to hypothermia.

12. A method of treating a neonate for complications associated with childbirth, the method comprising:
   administering the formulation according to claim 1 to a neonate in need thereof or to the neonate's mother, to treat the effects of complications during childbirth.

* * * * *

UNITED STATES PATENT AND TRADEMARK OFFICE
CERTIFICATE OF CORRECTION

PATENT NO. : 9,616,135 B2
APPLICATION NO. : 14/676419
DATED : April 11, 2017
INVENTOR(S) : Paul W. T. J. Leufkens It is certified that error appears in the above-identified patent and that said Letters Patent is hereby corrected as shown below:

In the Specification
| | | |
|---|---|---|
| Column 6, | Line 29, | change "the 2-1B formulations" to --the 2-IB formulations-- |
| Column 15, | Lines 19-20, | change "(3-cyclodextrin)" to --β-cyclodextrin)-- |
| Column 23, | Line 23, | change "24B-citrate buffer" to --2-IB-citrate buffer-- |
| Column 23, | Line 34, | change "buffer foundations," to --buffer formulations,-- |

In the Claims
| | | | |
|---|---|---|---|
| Claim 1, | Column 45, | Line 34, | change "hydroxyipropyl-beta" to --hydroxylpropyl-beta-- |

Signed and Sealed this
Thirtieth Day of January, 2018

Joseph Matal
*Performing the Functions and Duties of the
Under Secretary of Commerce for Intellectual Property and
Director of the United States Patent and Trademark Office*